(12) United States Patent
Lattimore et al.

(10) Patent No.: US 10,765,561 B2
(45) Date of Patent: *Sep. 8, 2020

(54) SYSTEMS AND METHODS FOR USING NEGATIVE PRESSURE WOUND THERAPY TO MANAGE OPEN ABDOMINAL WOUNDS

(71) Applicant: Smith & Nephew, Inc., Memphis, TN (US)

(72) Inventors: James D. Lattimore, Safety Harbor, FL (US); Michael B. Mosholder, Palm Harbor, FL (US)

(73) Assignee: Smith & Nephew, Inc., Memphis, TN (US)

( * ) Notice: Subject to any disclaimer, the term of this patent is extended or adjusted under 35 U.S.C. 154(b) by 828 days.

This patent is subject to a terminal disclaimer.

(21) Appl. No.: 14/333,125

(22) Filed: Jul. 16, 2014

(65) Prior Publication Data

US 2015/0011954 A1 Jan. 8, 2015

Related U.S. Application Data

(63) Continuation of application No. 12/886,088, filed on Sep. 20, 2010, now Pat. No. 8,791,315.

(Continued)

(51) Int. Cl.
*A61F 13/15* (2006.01)
*A61F 13/00* (2006.01)
(Continued)

(52) U.S. Cl.
CPC .. *A61F 13/00021* (2013.01); *A61F 13/00017* (2013.01); *A61F 13/00068* (2013.01);
(Continued)

(58) Field of Classification Search
CPC ........ A61F 13/15; A61F 13/148; A61F 13/14; A61F 13/00068; A61F 13/00038;
(Continued)

(56) References Cited

U.S. PATENT DOCUMENTS

| 1,066,934 A | 7/1913 | Manney |
| 4,095,599 A | 6/1978 | Simonet-Haibe |

(Continued)

FOREIGN PATENT DOCUMENTS

| DE | 3 539 533 | 5/1987 |
| EP | 0 122 085 | 6/1987 |

(Continued)

OTHER PUBLICATIONS

U.S. Appl. No. 29/363,038, filed Jun. 30, 2010, Lattimore et al.

(Continued)

*Primary Examiner* — Rachael E Bredefeld
*Assistant Examiner* — Camtu T Nguyen
(74) *Attorney, Agent, or Firm* — Knobbe, Martens, Olson & Bear, LLP

(57) ABSTRACT

Embodiments disclosed herein are directed to the treatment of wounds using negative pressure. Some embodiments disclosed herein provide for a foam pad, which may be suitable for use in abdominal wound sites, and which may be sized in a dimensionally-independent manner. Additional embodiments provide for a wound contact layer, as well as a system for the treatment of abdominal wounds.

14 Claims, 36 Drawing Sheets

Related U.S. Application Data

(60) Provisional application No. 61/308,766, filed on Feb. 26, 2010.

(51) Int. Cl.
*A61M 1/00* (2006.01)
*A61F 13/06* (2006.01)

(52) U.S. Cl.
CPC ......... *A61M 1/0088* (2013.01); *A61F 13/069* (2013.01); *A61F 2013/0054* (2013.01); *A61F 2013/0074* (2013.01); *A61F 2013/00157* (2013.01); *A61F 2013/00174* (2013.01); *A61F 2013/00251* (2013.01); *A61F 2013/00255* (2013.01); *A61F 2013/00519* (2013.01); *A61F 2013/00536* (2013.01); *A61F 2013/00812* (2013.01); *A61F 2013/00842* (2013.01); *A61F 2013/00859* (2013.01); *A61F 2013/00863* (2013.01); *A61M 2210/1021* (2013.01)

(58) Field of Classification Search
CPC ................. A61F 13/00046; A61F 5/03; A61F 2013/00217; A61F 13/00021; A61F 13/00017; A61F 13/069; A61F 2013/00157; A61F 2013/00251; A61F 2013/00255; A61F 2013/00519; A61F 2013/00536; A61F 2013/0054; A61F 2013/0074; A61F 2013/00812; A61F 2013/00842; A61F 2013/00859; A61F 2013/00863; A61M 27/00; A61M 2210/1021
USPC .......... 604/304–305; 602/46; 128/95.1, 96.1, 128/112.1
See application file for complete search history.

(56) References Cited

U.S. PATENT DOCUMENTS

| | | |
|---|---|---|
| 4,252,119 A | 2/1981 | Coates |
| 4,341,207 A | 7/1982 | Steer et al. |
| 4,360,021 A | 11/1982 | Stima |
| 4,499,896 A | 2/1985 | Heinecke |
| 4,541,426 A * | 9/1985 | Webster ............ A61F 13/00034 602/42 |
| 4,561,435 A | 12/1985 | McKnight et al. |
| 4,690,134 A * | 9/1987 | Snyders .............. A61M 1/1068 601/153 |
| 4,699,134 A * | 10/1987 | Samuelsen .......... A61F 13/0253 602/42 |
| 4,759,354 A | 7/1988 | Quarfoot |
| 4,798,603 A | 1/1989 | Meyer et al. |
| 4,867,150 A | 9/1989 | Gilbert |
| 4,875,473 A | 10/1989 | Alvarez |
| 4,882,213 A | 11/1989 | Gaddis et al. |
| 4,969,880 A | 11/1990 | Zamierowski |
| 4,997,425 A | 3/1991 | Shioya et al. |
| 5,080,661 A | 1/1992 | Lavender et al. |
| 5,149,331 A | 9/1992 | Ferdman et al. |
| 5,218,973 A | 6/1993 | Weaver et al. |
| 5,261,893 A | 11/1993 | Zamierowski |
| 5,264,218 A * | 11/1993 | Rogozinski ........... A61F 13/023 424/443 |
| 5,322,695 A | 6/1994 | Shah et al. |
| 5,336,209 A | 8/1994 | Porzilli |
| 5,445,604 A | 8/1995 | Lang |
| 5,486,158 A | 1/1996 | Samuelson |
| 5,496,605 A | 3/1996 | Augst et al. |
| 5,527,293 A | 6/1996 | Zamierowski |
| 5,549,584 A | 8/1996 | Gross |
| 5,593,395 A | 1/1997 | Martz |
| 5,599,289 A | 2/1997 | Castellana |
| 5,616,387 A | 4/1997 | Augst et al. |
| 5,633,007 A | 5/1997 | Webb et al. |
| 5,636,643 A | 6/1997 | Argenta et al. |
| 5,645,081 A | 7/1997 | Argenta et al. |
| 5,681,579 A | 10/1997 | Freeman |
| 5,713,881 A | 2/1998 | Rezai et al. |
| 5,714,225 A | 2/1998 | Hansen et al. |
| 5,733,305 A | 3/1998 | Fleischmann |
| 5,759,570 A | 6/1998 | Arnold |
| 5,792,090 A | 8/1998 | Ladin |
| 5,810,755 A | 9/1998 | LeVeen et al. |
| D403,774 S | 1/1999 | Laughlin et al. |
| 5,885,237 A | 3/1999 | Kadash et al. |
| D408,920 S | 4/1999 | Dunshee et al. |
| 5,899,893 A | 5/1999 | Dyer et al. |
| 5,958,420 A | 9/1999 | Jenson |
| D415,836 S | 10/1999 | Dunshee et al. |
| 5,981,822 A | 11/1999 | Addison |
| 5,985,990 A | 11/1999 | Kantner et al. |
| 6,071,267 A | 6/2000 | Zamierowski |
| 6,087,549 A | 7/2000 | Flick |
| 6,117,111 A | 9/2000 | Fleischmann |
| 6,142,982 A | 11/2000 | Hunt et al. |
| 6,203,563 B1 | 3/2001 | Fernandez |
| 6,293,281 B1 | 9/2001 | Shultz et al. |
| 6,345,623 B1 | 2/2002 | Heaton et al. |
| 6,350,339 B1 | 2/2002 | Sessions |
| 6,398,767 B1 | 6/2002 | Fleischmann |
| 6,458,109 B1 | 10/2002 | Henley et al. |
| 6,553,998 B2 | 4/2003 | Heaton et al. |
| 6,680,113 B1 | 1/2004 | Lucast et al. |
| 6,685,681 B2 | 2/2004 | Lockwood et al. |
| 6,695,823 B1 | 2/2004 | Lina et al. |
| 6,752,794 B2 | 6/2004 | Lockwood et al. |
| 6,794,554 B2 | 9/2004 | Sessions et al. |
| 6,797,855 B2 | 9/2004 | Worthley |
| 6,814,079 B2 | 11/2004 | Heaton et al. |
| 6,838,589 B2 | 1/2005 | Liedtke et al. |
| 6,855,135 B2 | 2/2005 | Lockwood et al. |
| D506,547 S | 6/2005 | Cruz et al. |
| 6,951,553 B2 | 10/2005 | Bubb et al. |
| 6,974,428 B2 | 12/2005 | Knutson et al. |
| 7,004,915 B2 | 2/2006 | Boynton et al. |
| 7,005,556 B1 | 2/2006 | Becker et al. |
| 7,030,288 B2 | 4/2006 | Liedtke et al. |
| 7,041,868 B2 | 5/2006 | Greene et al. |
| 7,137,968 B1 | 11/2006 | Burrell et al. |
| D537,948 S | 3/2007 | Smith |
| D544,607 S | 6/2007 | Henry et al. |
| 7,291,762 B2 | 11/2007 | Flick |
| 7,335,809 B2 | 2/2008 | Riesinger |
| 7,338,482 B2 | 3/2008 | Lockwood et al. |
| 7,381,859 B2 | 6/2008 | Hunt et al. |
| 7,518,031 B2 | 4/2009 | Liedtke et al. |
| 7,540,848 B2 | 6/2009 | Hannigan et al. |
| 7,645,269 B2 | 1/2010 | Zamierowski |
| 7,722,582 B2 | 5/2010 | Lina et al. |
| D622,122 S | 7/2010 | Cotton |
| D622,123 S | 7/2010 | Igwebuike |
| 7,790,946 B2 | 9/2010 | Mulligan |
| 7,794,438 B2 | 9/2010 | Henley et al. |
| D639,441 S | 6/2011 | Sferle |
| D644,330 S | 8/2011 | Pfeiffer et al. |
| RE43,195 E | 2/2012 | Cotton |
| 8,791,315 B2 * | 7/2014 | Lattimore ......... A61F 13/00021 602/43 |
| 2001/0027285 A1 | 10/2001 | Heinecke et al. |
| 2001/0034499 A1 * | 10/2001 | Sessions ........... A61F 13/00021 602/46 |
| 2002/0065494 A1 | 5/2002 | Lockwood et al. |
| 2002/0082567 A1 | 6/2002 | Lockwood et al. |
| 2002/0161346 A1 | 10/2002 | Lockwood et al. |
| 2004/0006319 A1 | 1/2004 | Lina et al. |
| 2004/0064111 A1 | 4/2004 | Lockwood et al. |
| 2004/0162512 A1 | 8/2004 | Liedtke et al. |
| 2005/0113733 A1 | 5/2005 | Liedtke et al. |
| 2005/0131327 A1 | 6/2005 | Lockwood et al. |
| 2005/0143697 A1 | 6/2005 | Riesinger |
| 2005/0181163 A1 | 8/2005 | Kose |
| 2006/0041247 A1 | 2/2006 | Petrosenko et al. |

(56) References Cited

U.S. PATENT DOCUMENTS

| | | | |
|---|---|---|---|
| 2006/0142687 A1 | 6/2006 | Liedtke et al. | |
| 2006/0178608 A1 | 8/2006 | Stapf | |
| 2006/0241689 A1 | 10/2006 | Leiboff et al. | |
| 2007/0142761 A1 | 6/2007 | Aali | |
| 2008/0095979 A1 | 4/2008 | Hatanaka et al. | |
| 2008/0213344 A1 | 9/2008 | McCarthy et al. | |
| 2008/0243044 A1 | 10/2008 | Hunt et al. | |
| 2009/0099519 A1* | 4/2009 | Kaplan | A61F 7/12 604/113 |
| 2009/0130186 A1 | 5/2009 | McCarthy et al. | |
| 2009/0177136 A1 | 7/2009 | Liedtke et al. | |
| 2009/0227969 A1 | 9/2009 | Jaeb et al. | |
| 2009/0240185 A1* | 9/2009 | Jaeb | A61M 1/0088 602/48 |
| 2010/0069829 A1 | 3/2010 | Hutchinson et al. | |
| 2010/0069858 A1 | 3/2010 | Olson | |
| 2010/0069885 A1 | 3/2010 | Stevenson et al. | |
| 2010/0100022 A1 | 4/2010 | Greener et al. | |
| 2010/0106115 A1 | 4/2010 | Hardman et al. | |
| 2010/0106117 A1 | 4/2010 | Lockwood et al. | |
| 2011/0178451 A1 | 7/2011 | Robinson et al. | |
| 2011/0213287 A1 | 9/2011 | Lattimore et al. | |
| 2014/0228787 A1 | 8/2014 | Croizat et al. | |
| 2016/0022500 A1* | 1/2016 | Tumey | A61M 1/0088 604/319 |

FOREIGN PATENT DOCUMENTS

| | | |
|---|---|---|
| EP | 0 418 607 | 3/1991 |
| EP | 0 485 657 | 5/1992 |
| EP | 0 617 938 | 3/1994 |
| EP | 0 638 301 | 2/1995 |
| EP | 0 670 705 | 9/1995 |
| EP | 0 465 601 | 1/1997 |
| EP | 0 762 860 | 3/1997 |
| EP | 0 651 983 | 9/1998 |
| EP | 0 777 504 | 10/1998 |
| EP | 0 688 189 | 9/2000 |
| EP | 0 865 304 | 7/2001 |
| EP | 0 875 222 | 7/2002 |
| EP | 0 853 950 | 10/2002 |
| EP | 1 513 478 | 4/2003 |
| EP | 1 088 569 | 8/2003 |
| EP | 1 219 311 | 7/2004 |
| EP | 1 018 967 | 8/2004 |
| EP | 1 440 667 | 3/2006 |
| EP | 1 284 777 | 4/2006 |
| EP | 1 620 720 | 11/2006 |
| EP | 1 772 160 | 6/2009 |
| EP | 2 214 728 | 8/2010 |
| EP | 2 538 902 | 9/2015 |
| GB | 1063066 | 3/1967 |
| GB | 2085305 | 1/1985 |
| GB | 2329127 | 3/1999 |
| GB | 2305610 | 7/1999 |
| GB | 2357286 | 11/2003 |
| GB | 2389794 | 12/2003 |
| GB | 2365350 | 8/2004 |
| GB | 2423019 | 8/2006 |
| JP | 2008-73187 | 4/2008 |
| WO | WO 1992/13713 | 8/1992 |
| WO | WO 1993/00056 | 1/1993 |
| WO | WO 1994/20041 | 9/1994 |
| WO | WO 1996/24316 | 8/1996 |
| WO | WO 1997/43991 | 11/1997 |
| WO | WO 1998/38955 | 9/1998 |
| WO | WO 2000/07653 | 2/2000 |
| WO | WO 2000/21586 | 4/2000 |
| WO | WO 2000/61206 | 10/2000 |
| WO | WO 2001/49233 | 7/2001 |
| WO | WO 2001/85248 | 11/2001 |
| WO | WO 2002/05737 | 1/2002 |
| WO | WO 2002/26180 | 4/2002 |
| WO | WO 2002/39940 | 5/2002 |
| WO | WO 2002/41878 | 5/2002 |
| WO | WO 2002/45761 | 6/2002 |
| WO | WO 2002/091965 | 11/2002 |
| WO | WO 2003/086232 | 10/2003 |
| WO | WO 2004/018020 | 3/2004 |
| WO | WO 2005/009488 | 2/2005 |
| WO | WO 2006/130594 | 12/2006 |
| WO | WO 2007/075379 | 7/2007 |
| WO | WO 2008/039839 | 4/2008 |
| WO | WO 2008/040681 | 4/2008 |
| WO | WO 2008/064503 | 6/2008 |
| WO | WO 2008/104609 | 9/2008 |
| WO | WO 2009/011856 | 1/2009 |
| WO | WO 2009/021523 | 2/2009 |
| WO | WO 2009/070905 | 6/2009 |
| WO | WO 2009/135171 | 11/2009 |
| WO | WO 2009/156949 | 12/2009 |
| WO | WO 2009/158131 | 12/2009 |
| WO | WO 2010/016791 | 2/2010 |
| WO | WO 2010/033271 | 3/2010 |
| WO | WO 2010/033574 | 3/2010 |
| WO | WO 2010/033613 | 3/2010 |
| WO | WO 2010/051068 | 5/2010 |
| WO | WO 2010/051073 | 5/2010 |
| WO | WO 2010/072309 | 7/2010 |
| WO | WO 2011/106722 | 9/2011 |
| WO | WO 2012/138514 | 10/2012 |

OTHER PUBLICATIONS

U.S. Appl. No. 12/443,169, filed Nov. 17, 2009, published as 2010/0100022, including its ongoing prosecution history, including without limitation Office Actions, Amendments, Remarks, and any other potentially relevant documents, U.S. Pat. No. 8,680,360, Apr. 22, 2010, Greener et al.

U.S. Appl. No. 12/886,088, filed Sep. 20, 2010, including its ongoing prosecution history, including without limitation Office Actions, Amendments, Remarks, and any other potentially relevant documents, now U.S. Pat. No. 8,791,315, Sep. 1, 2011, Lattimore, et al.

"Hydrocolloids," J. of Wound Care, vol. 1, No. 2, (Jul.-Aug. 1992), pp. 27-30.

Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).

Barker et al., "Vacuum Pack Technique of Temporary Abdominal Closure"; J. of Traumatic Injury, Infection, and Critical Care, vol. 48, No. 2 (2000).

Brock, W.B., et al.: "Temporary closure of open abdominal wounds: the vacuum pack", Am. Surg. Jan. 1995; 61(1)30-5—abstract.

Fleischmann, W., et al. "Vacuum Sealing for Treatment of Soft Tissue Injury in Open Fractures," Emergency Surgery (1993) 96:488-492.

Garner et al., "Vacuum-assisted wound closure provides early fascial reapproximation in trauma patients with open abdomens," Am. J. of Surgery 1282 (2001) 630-638.

Harris, "A new technique of skin grafting using Stei-Greffe and a self-adhering foam pad," Brit. J. of Plastic Surg., vol. 34, No. 2, (Apr. 1981), pp. 181-185.

International Preliminary Report on Patentability and Written Opinion for International Application No. PCT/US2011/026347 (published WO 2011/106722), dated Aug. 28, 2012.

International Search Report for International Application No. PCT/US2011/026347 (published WO 2011/106722), dated Jun. 6, 2011.

Jeter, K. "Managing Draining Wounds and Fistulae: New and Established Methods" Chronic Wound Care pp. 240-246, 1990.

KCI Licensing, "V.A.C. Abdominal Dressing System Advanced Management of the Open Abdomen," 2004.

Navsaria, et al.: "Temporary closure of open abdominal wounds by the modified sandwich-vacuum pack technique", British Journal of Surgery 2003; 90: 718-722.

(56) References Cited

OTHER PUBLICATIONS

Nicholas, J.M., Options for Management of the Open Abdomen, Presentation from Emory University School of Medicine, 66 pgs. Invited Speaker American College of Surgeons 32nd Annual Spring Meeting, General Session 12—Presentation and Panel Discussion on the Open Abdomen in General Surgery—How Do You Close the Abdomen When You Can't—Bostom Marriott Copley Place Hotel, Boston, MA Apr. 26, 2004.

Orgill, D.P., et al., Guidelines for Treatment of Complex Chest Wounds with Negative Pressure Wound Therapy, *Wounds, A Compendium of Clinical Research and Practice*, Suppl. B, Dec. 2004, 1-23.

Schein et al., "The 'Sandwich Technique' in the Management of the Open Abdomen," British Journal of Surger, 1986, vol. 73, May, pp. 369-370.

Smith, et al.; Vacuum Pack Technique of Temporary Abdominal Closure: A Four-Year Experience; The American Surgeon; Dec. 1997; p. 1102-1108; vol. 63, No. 12.

Solovev, V.A. "Treatment and Prevention of Suture Failures after Gastric Resection" (Dissertation Abstract) (S.M. Kirov Gorky State Medical Institute, Gorky USSR 1988).

Australian First Office Action, re AU Application No. 2011220389, dated Feb. 22, 2014.

Canadian Office Action, re CA Application No. 2,790,392, dated Nov. 4, 2016.

Chinese Office Action and Search Report re CN Application No. 201180011292.3, dated Feb. 27, 2014.

Chinese Second Office Action re CN Application No. 201180011292.3, dated Nov. 4, 2014.

Chinese Third Office Action, re CN Application No. 201180011292.3, dated May 22, 2015.

European Exam Report Re EPO Application No. 11 706 727.2, dated Jan. 20, 2014.

Japanese Second Office Action, re JP Application No. 2012-555197, dated Aug. 17, 2015.

Japanese First Office Action, re JP Application No. 2015-030349, dated Jan. 18, 2016.

Japanese Office Action, re JP Application No. 2015-030349, dated Sep. 12, 2016.

Japanese Office Action, re JP Application No. 2012-555197, dated Nov. 25, 2014.

KCI V.A.C. Simplace Dressing Brochure 2008, in 2 pages.

Mexican Office Action, re MX Application No. MX/a/2012/009864, dated Jul. 28, 2016.

\* cited by examiner

103

SYSTEMS AND METHODS FOR USING NEGATIVE PRESSURE WOUND THERAPY TO MANAGE OPEN ABDOMINAL WOUNDS

CROSS REFERENCE TO RELATED APPLICATIONS

This application is a continuation of U.S. patent application Ser. No. 12/886,088, filed on Sep. 20, 2010, now U.S. Pat. No. 8,791,315, entitled "SYSTEMS AND METHODS FOR USING NEGATIVE PRESSURE WOUND THERAPY TO MANAGE OPEN ABDOMINAL WOUNDS," which claims the benefit of U.S. Provisional Application No. 61/308,766, filed on Feb. 26, 2010, entitled "FOAM PAD FOR USE IN NEGATIVE PRESSURE WOUND THERAPY." The contents of the aforementioned applications are hereby incorporated by reference in their entireties as if fully set forth herein. The benefit of priority to the foregoing applications is claimed under the appropriate legal basis, including, without limitation, under 35 U.S.C. § 119(e).

BACKGROUND

Field of Use

Embodiments of the present invention relate generally to the treatment of wounds using negative pressure wound therapy, and more specifically to an improved apparatus and method thereof to manage open abdominal wounds.

Description of Related Art

The treatment of open or chronic wounds by means of applying negative pressure to the site of the wound, where the wounds are too large to spontaneously close or otherwise fail to heal is well known in the art. Negative pressure wound treatment systems currently known in the art commonly involve placing a cover that is impermeable to liquids over the wound, using various mechanisms to seal the cover to the tissue of the patient surrounding the wound, and connecting a source of negative pressure (such as a vacuum pump) to the cover whereby an area of negative pressure is created under the cover in the area of the wound.

SUMMARY

Embodiments of the invention disclosed herein are directed to a reduced pressure appliance and methods of treatment using a reduced pressure appliance, and may be useful in the treatment of wounds using reduced pressure.

Certain embodiments of the invention are directed to improved methods of treating abdominal wounds or incisions with negative pressure. For example and for illustrative purposes only, some embodiments employ a porous pad with detachable sections permitting desired sizing of the pad to the wound site. Sizing of the foam pad may in some embodiments be performed in a dimensionally-independent manner so that, for example, the width and/or length may be modified independently of each other. Further embodiments also provide for a wound contact layer to be placed in contact with the wound site, where the wound contact layer is preferably minimally or non-adherent to the wound site and provided with slits or other openings for the removal of wound exudate or fluids and the application of negative pressure to the wound site.

Certain embodiments provide for a negative pressure treatment system comprising a wound contact layer placed over the wound, a porous pad configured to be sized and positioned over the wound contact layer, a flexible drape configured to be placed above the wound and sealed to the skin surrounding the wound, and which further comprises a conduit configured to deliver negative pressure to the wound through an aperture in the flexible drape and through the porous pad and wound contact layer.

In a preferred embodiment, a porous pad is provided for the treatment of wounds with negative pressure, wherein the porous pad is comprised of a porous material suitable for channeling wound exudate from a wound site to a source of negative pressure. The porous pad preferably comprises a generally planar shape with a thickness less than its width and length, and preferably comprises at least one cut extending through a least a portion of the thickness of the pad, whereby the cut defines a pad section detachable from the remainder of the pad so as to permit modification of the size of the pad (for example its length and/or width). In certain embodiments, the cuts may be comprised of arcuate and/or elliptical cuts, and may further comprise additional inner and outer cuts. In further embodiments, additional intermediate cuts may also be present.

In another preferred embodiment, a system for the treatment of a wound site comprises a wound contact layer provided with openings for channeling wound exudate and distributing negative pressure, a generally planar porous pad suitable for transmitting negative pressure to a wound site and comprising at least one cut extending through a portion of the pad's thickness so as to define a detachable pad, a flexible drape, a conduit, and a source of negative pressure configured to deliver negative pressure through the conduit to the wound site.

In yet another preferred embodiment, a method of treating a wound site using negative pressure may comprise placing a wound contact layer onto the wound site; placing a porous pad over the wound contact layer, where the porous pad is perforated to allow removal of pad portions so as to permit sizing of the pad in a dimensionally-independent manner to fit the wound site; sealing the wound site with a flexible drape configured to be positioned over the wound and sealed to the skin surrounding the wound; connecting a source of negative pressure to the wound site; and maintaining the application of negative pressure until the wound site has healed appropriately.

DETAILED DESCRIPTION OF THE PREFERRED EMBODIMENTS

Preferred embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using reduced pressure. Wounds and/or wound sites include, but are not limited to, open wounds, pressure sores, ulcers and burns. Open wounds and/or wound sites may also include incisions (e.g., abdominal incisions) or other openings, tears, or fistulas, for example, in the abdominal or peritoneal cavity. Treatment of such wounds can be performed using negative pressure wound therapy, wherein a reduced or negative pressure can be applied to the wound to facilitate and promote healing of the wound. It will also be appreciated that the negative pressure systems and methods as disclosed herein may be applied to other parts of the body, and are not necessarily limited to treatment of wounds.

Figure 1:
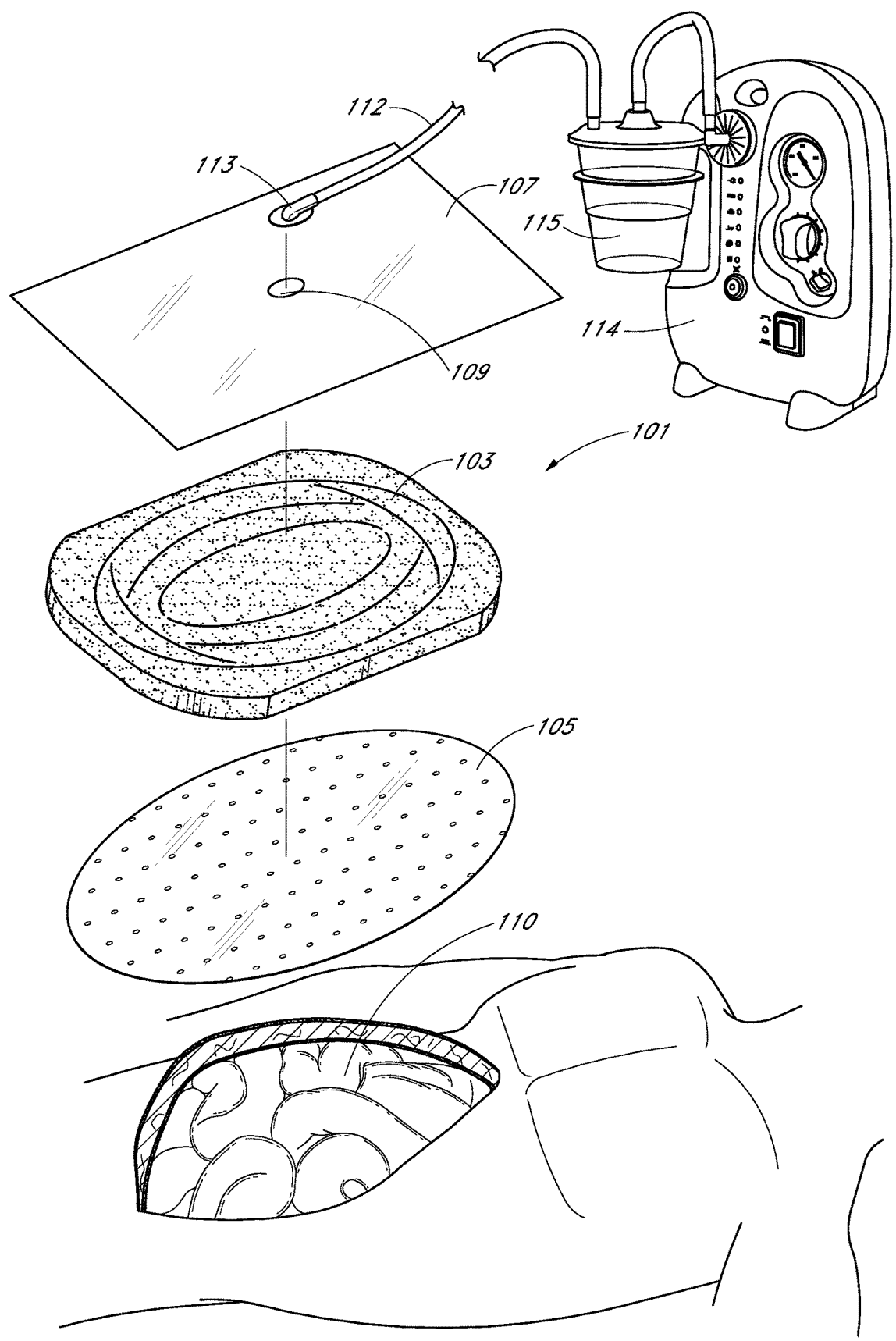
FIG. 1 is a schematic illustration of a system for the treatment of abdominal wounds.

Turning to FIG. 1, treatment of a wound with negative pressure in certain embodiments uses a negative pressure treatment system 101 as illustrated schematically here. In this embodiment, a wound site 110, illustrated here as an abdominal wound site, may benefit from treatment with negative pressure. Such abdominal wound sites may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening—particularly in the abdominal cavity—remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, preferably using the application of negative pressure, can be targeted to minimize the risk of infection, while promoting tissue viability and the removal of deleterious substances from the wound site. The application of reduced or negative pressure to a wound site has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, and/or enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached. Consequently, the application of negative pressure to a wound site 110 can be beneficial to a patient.

Accordingly, certain embodiments provide for a wound contact layer 105 to be placed over the wound site 110. Preferably, the wound contact layer 105 can be a thin, flexible material which will not adhere to the wound site or the exposed viscera in close proximity. For example, polymers such as polyurethane, polyethylene, polytetrafluoroethylene, or blends thereof may be used. In one embodiment, the wound contact layer is permeable. For example, the wound contact layer 105 can be provided with openings, such as holes, slits, or channels, to allow the removal of fluids from the wound site 110 or the transmittal of negative pressure to the wound site 110. Additional embodiments of the wound contact layer 105 are described in further detail below.

Certain embodiments of the negative pressure treatment system 101 may also use a porous pad 103, which can be disposed over the wound contact layer 105. This pad 103 can be constructed from a porous material, for example foam, that is soft, resiliently flexible, and generally conformable to the wound site 110. Such a foam can include an open-celled and reticulated foam made, for example, of a polymer. Suitable foams include foams composed of, for example, polyurethane, silicone, and polyvinyl alcohol. Preferably, this pad 103 can channel wound exudate and other fluids through itself when negative pressure is applied to the wound. Some pads 103 may include preformed channels or openings for such purposes. In certain embodiments, the pad 103 may have a thickness between about one inch and about two inches. The pad may also have a length of between about 16 and 17 inches, and a width of between about 11 and 12 inches. In other embodiments, the thickness, width, and/or length can have other suitable values. Other aspects of the pad 103 are discussed in further detail below.

Preferably, a drape 107 is used to seal the wound site 110. The drape 107 can be at least partially liquid impermeable, such that at least a partial negative pressure may be maintained at the wound site. Suitable materials for the drape 107 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the drape may be hydrophobic or hydrophilic. Examples of suitable materials include Transeal® available from DeRoyal and OpSite® available from Smith & Nephew. In order to aid patient comfort and avoid skin maceration, the drapes in certain embodiments are at least partly breathable, such that water vapor is able to pass through without remaining trapped under the dressing. An adhesive layer may be provided on at least a portion the underside of the drape 107 to secure the drape to the skin of the patient, although certain embodiments may instead use a separate adhesive or adhesive strip. Optionally, a release layer may be disposed over the adhesive layer to protect it prior to use and to facilitate handling the drape 107; in some embodiments, the release layer may be composed of multiple sections.

The negative pressure system 101 can be connected to a source of negative pressure, for example a pump 114. One example of a suitable pump is the Renasys EZ pump available from Smith & Nephew. The drape 107 may be connected to the source of negative pressure 114 via a conduit 112. The conduit 112 may be connected to a port 113 situated over an aperture 109 in the drape 107, or else the conduit 112 may be connected directly through the aperture 109 without the use of a port. In a further alternative, the conduit may pass underneath the drape and extend from a side of the drape. U.S. Pat. No. 7,524,315 discloses other similar aspects of negative pressure systems and is hereby incorporated by reference in its entirety and should be considered a part of this specification.

In many applications, a container or other storage unit 115 may be interposed between the source of negative pressure 114 and the conduit 112 so as to permit wound exudate and other fluids removed from the wound site to be stored without entering the source of negative pressure. Certain types of negative pressure sources—for example, peristaltic pumps—may also permit a container 115 to be placed after the pump 114. Some embodiments may also use a filter to prevent fluids, aerosols, and other microbial contaminants from leaving the container 115 and/or entering the source of negative pressure 114. Further embodiments may also include a shut-off valve or occluding hydrophobic and/or oleophobic filter in the container to prevent overflow; other embodiments may include sensing means, such as capacitative sensors or other fluid level detectors that act to stop or shut off the source of negative pressure should the level of fluid in the container be nearing capacity. At the pump exhaust, it may also be preferable to provide an odor filter, such as an activated charcoal canister.

Figure 2:
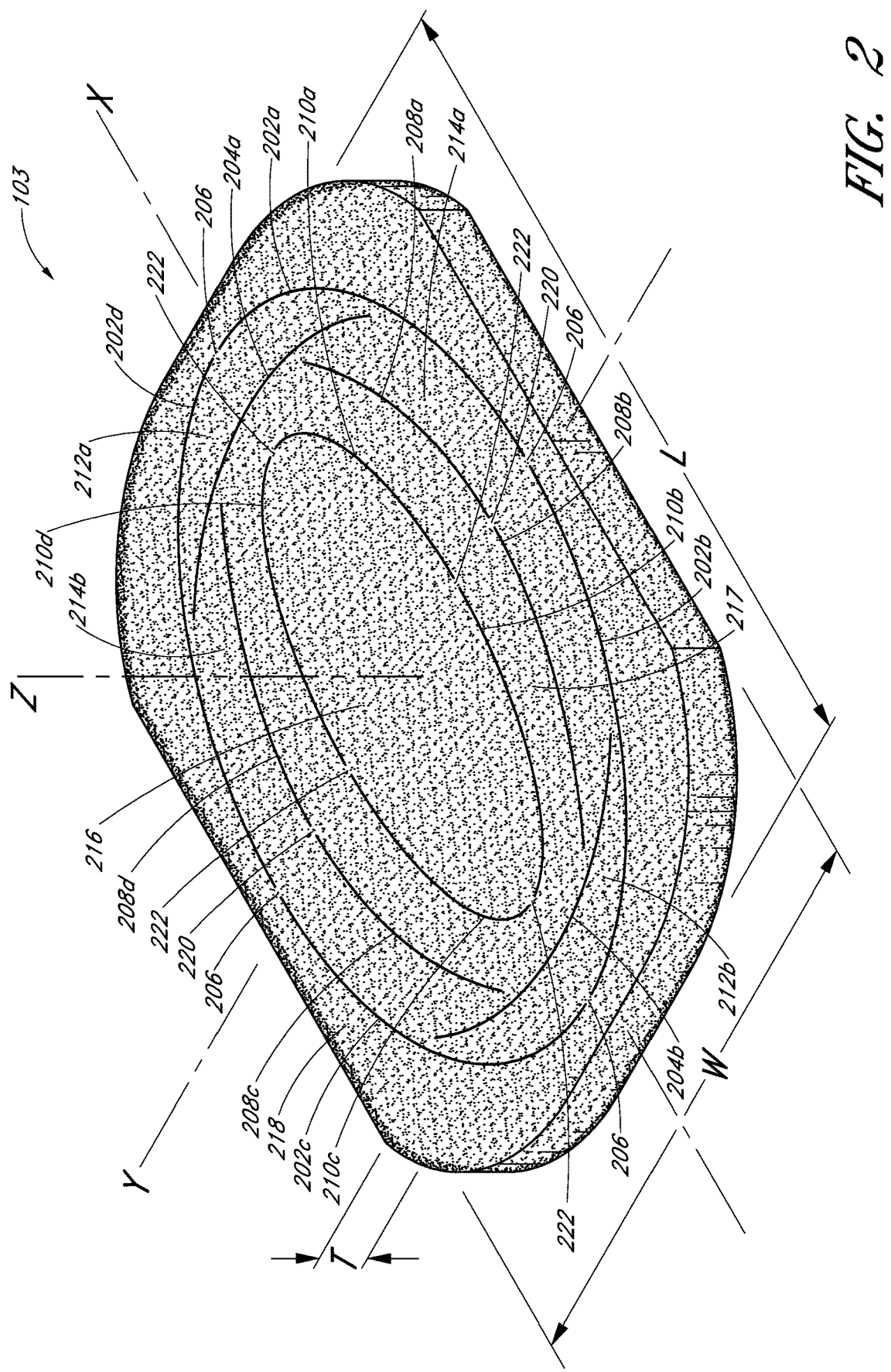
FIG. 2 illustrates a perspective view of one embodiment of a porous pad that can be used in the treatment of wounds.
Figure 3:
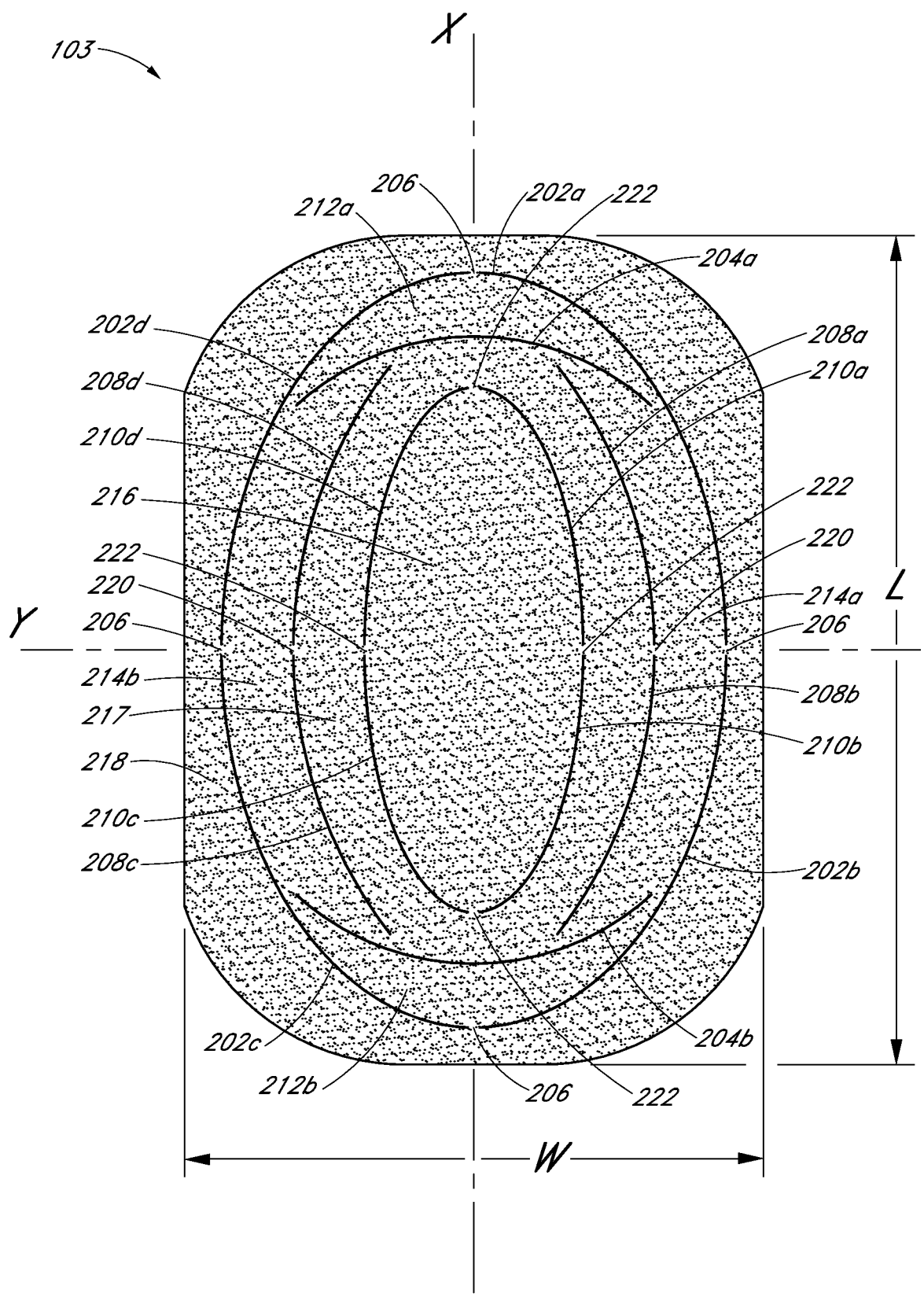
FIG. 3 illustrates a top view of the same porous pad.
Figure 4:
FIGS. 4-5 illustrate side views of the same porous pad.
Figure 5:
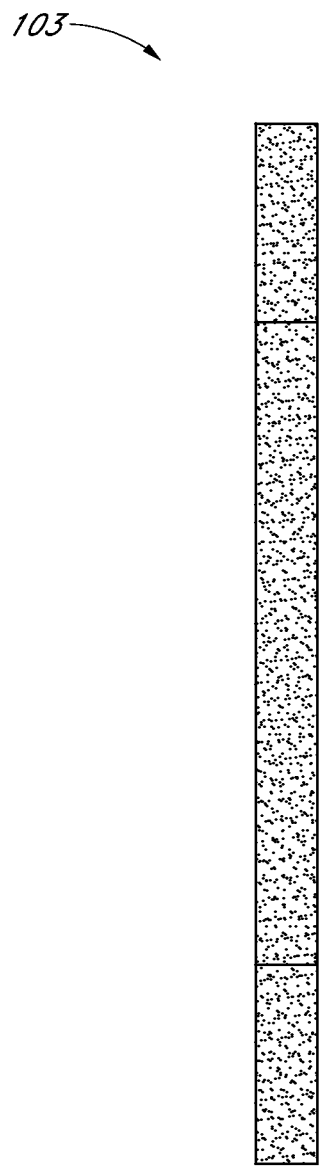
Figure 6:
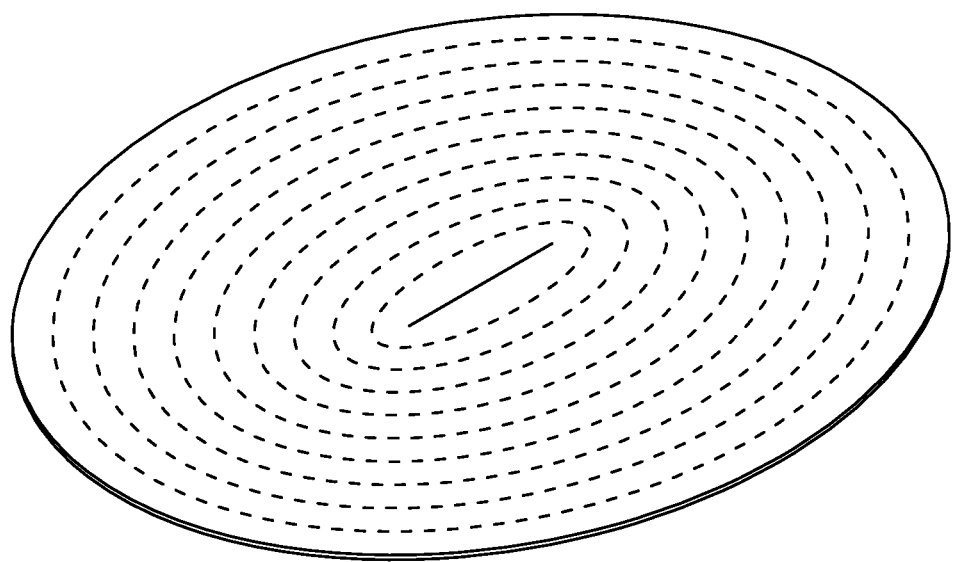
FIGS. 6-56 illustrate views of different embodiments of a wound contact layer.
Figure 7:
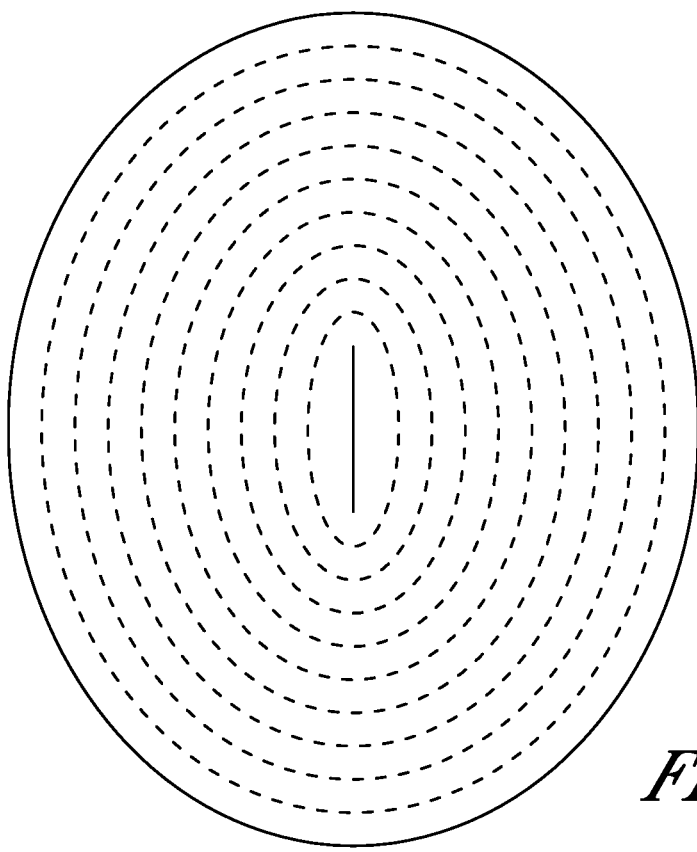
Figure 8:
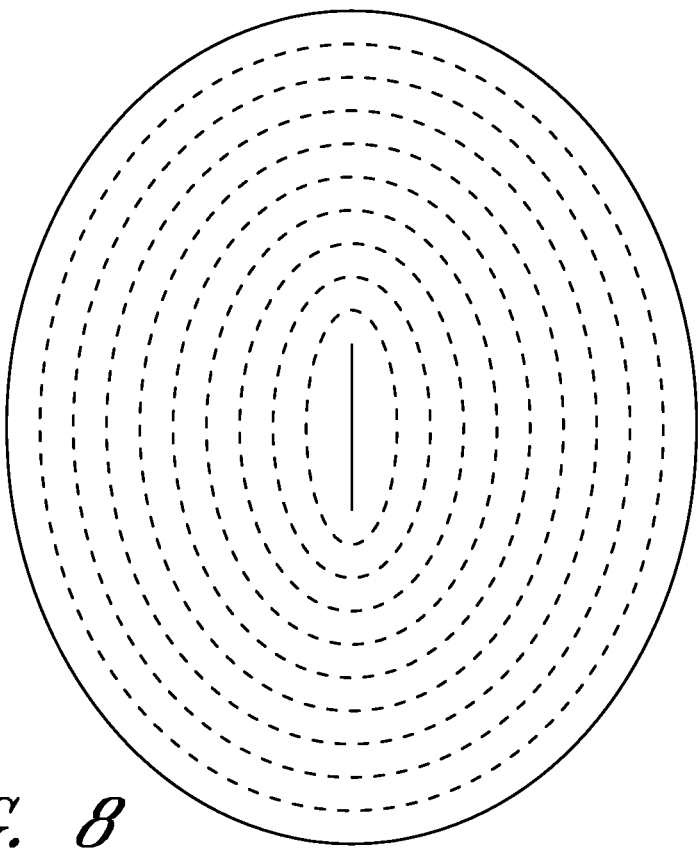
Figure 9:
Figure 10:
Figure 11:
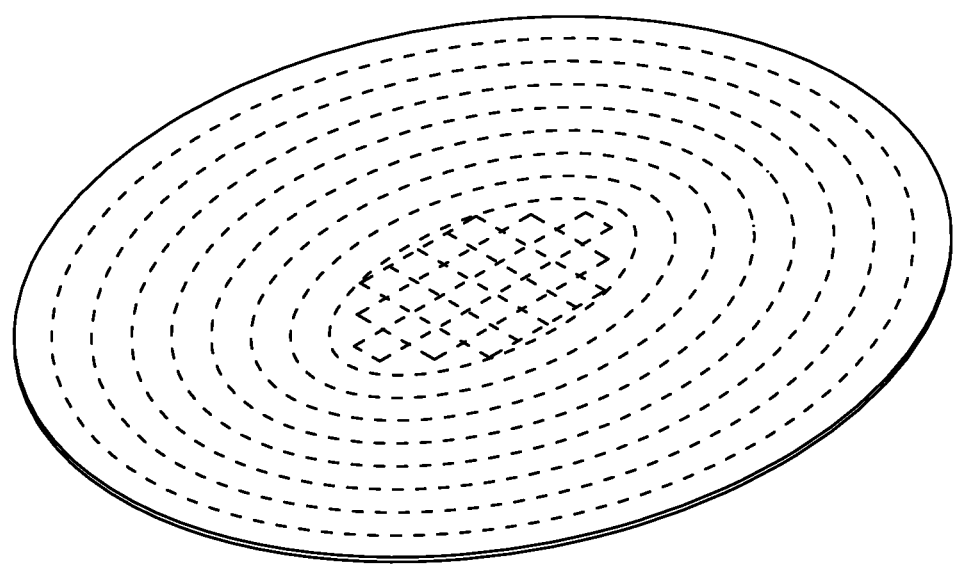
Figure 12:
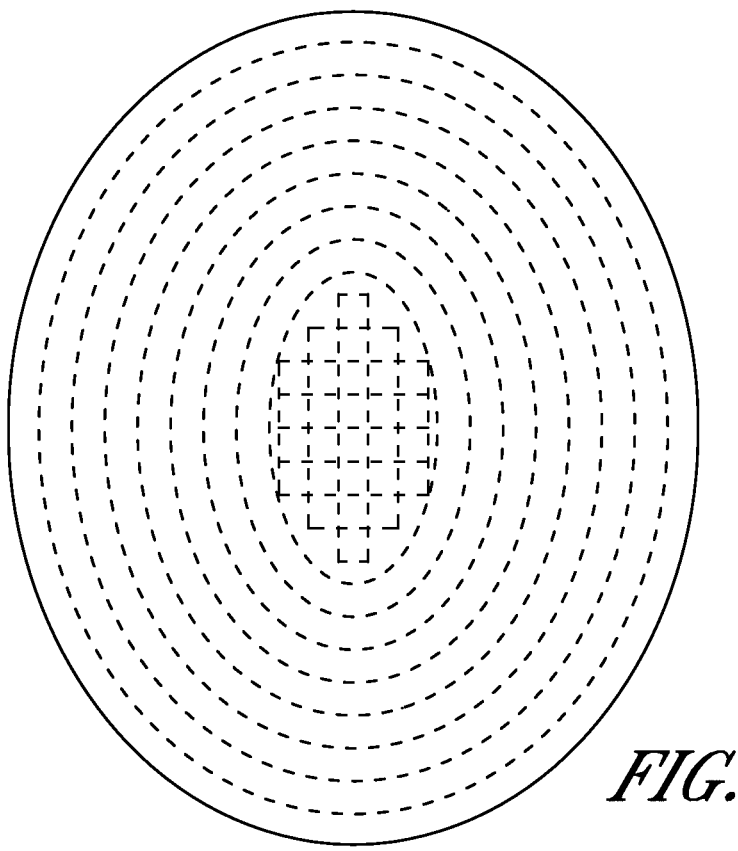
Figure 13:
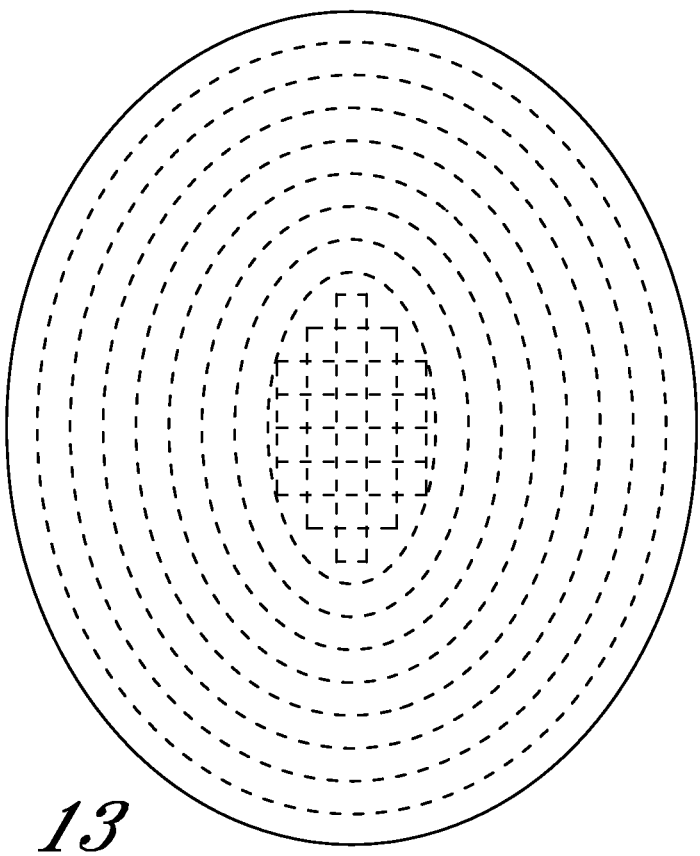
Figure 14:
Figure 15:
Figure 16:
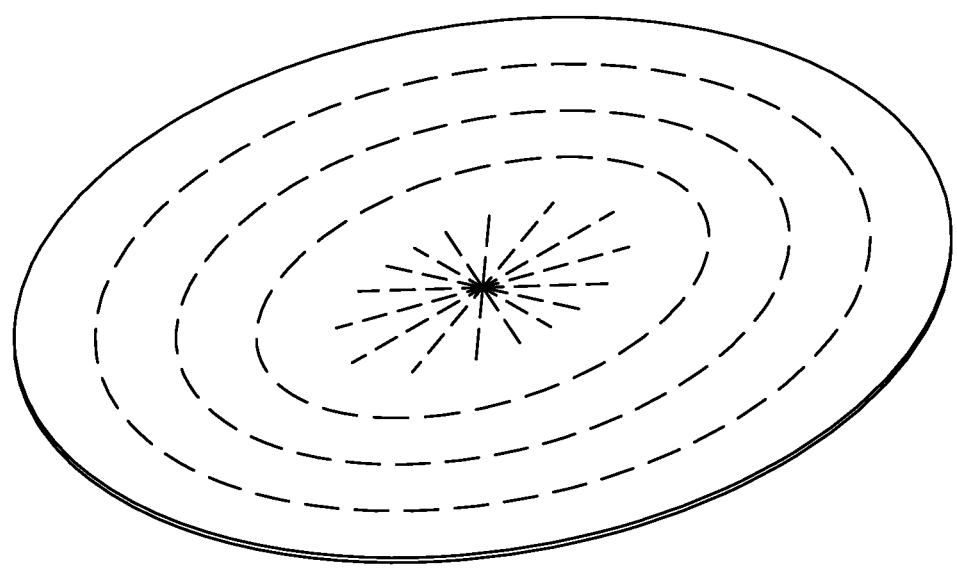
Figure 17:
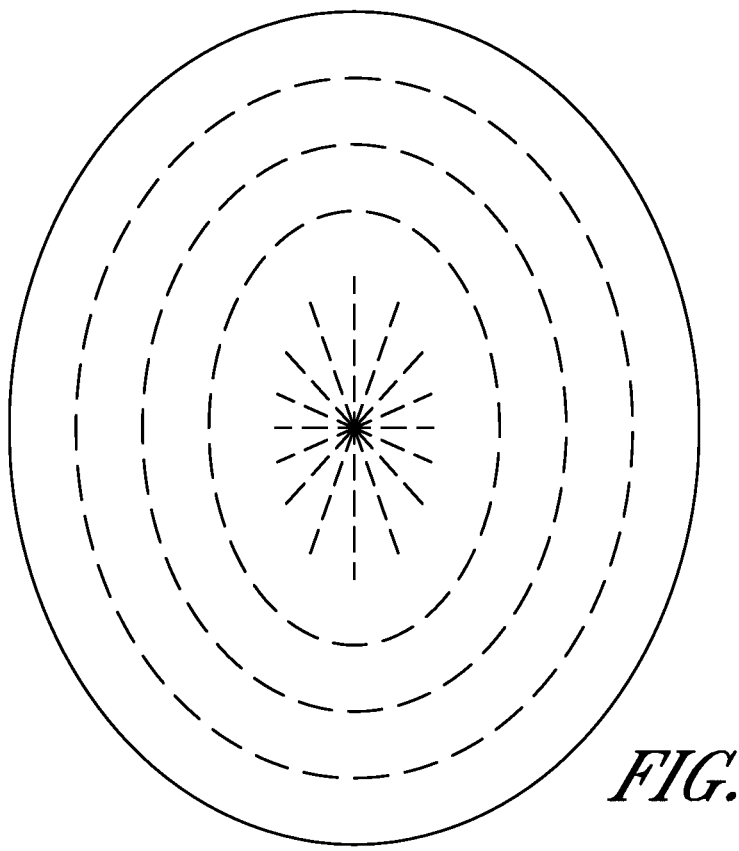
Figure 18:
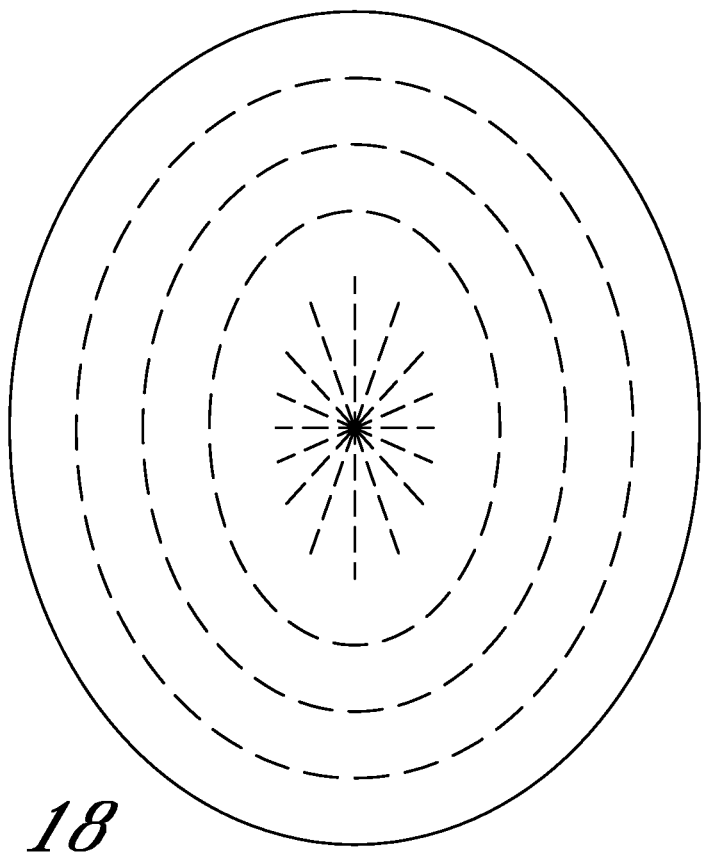
Figure 19:
Figure 20:
Figure 21:
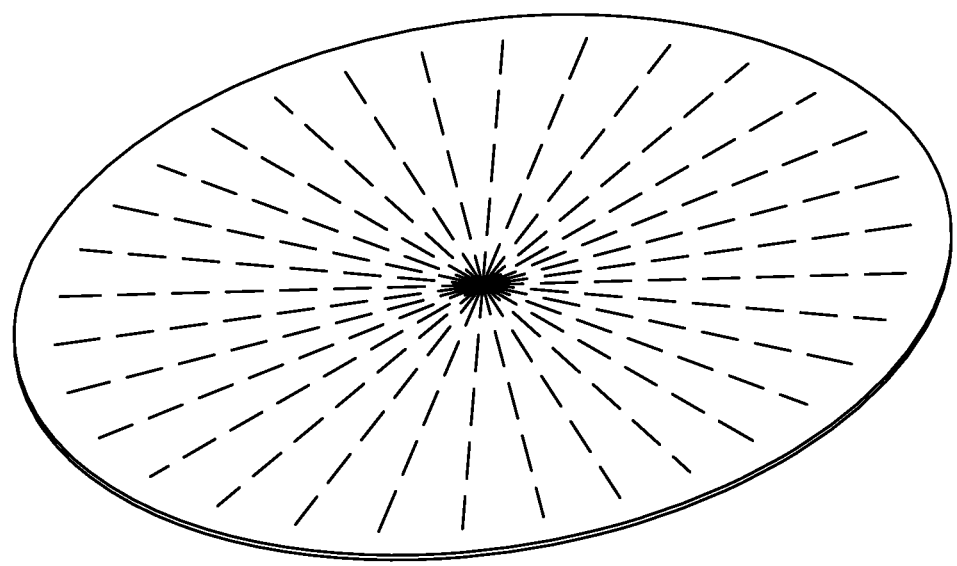
Figure 22:
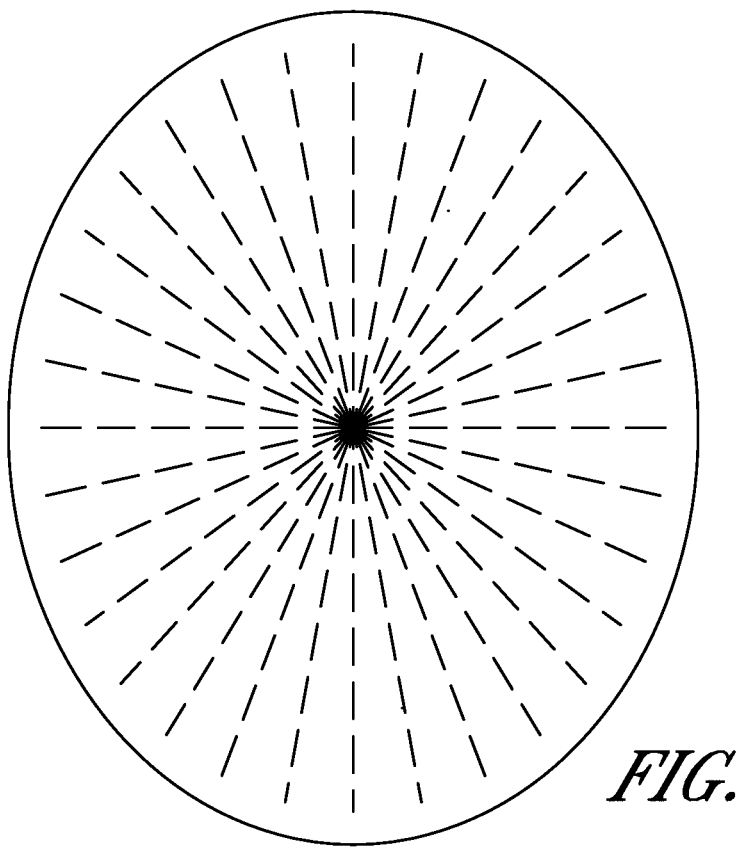
Figure 23:
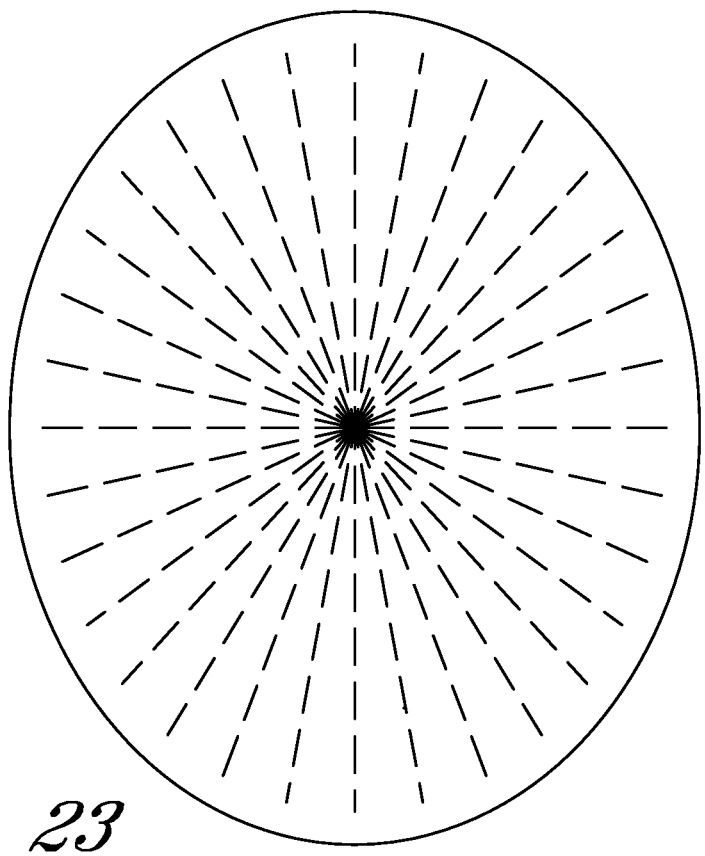
Figure 24:
Figure 25:
Figure 26:
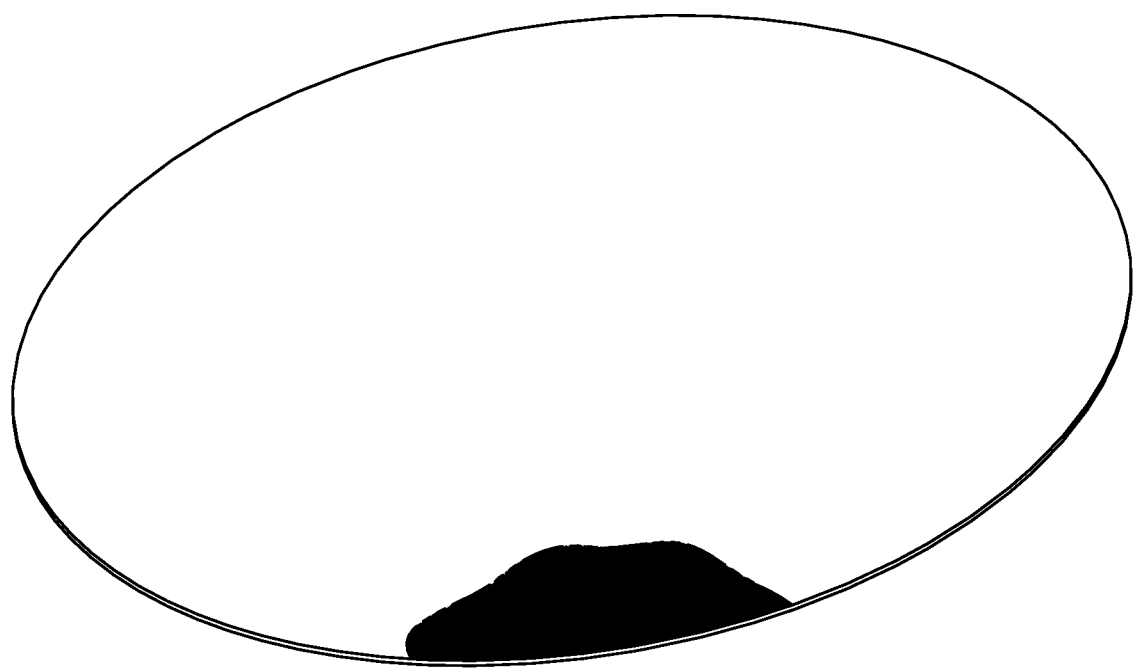
Figure 27:
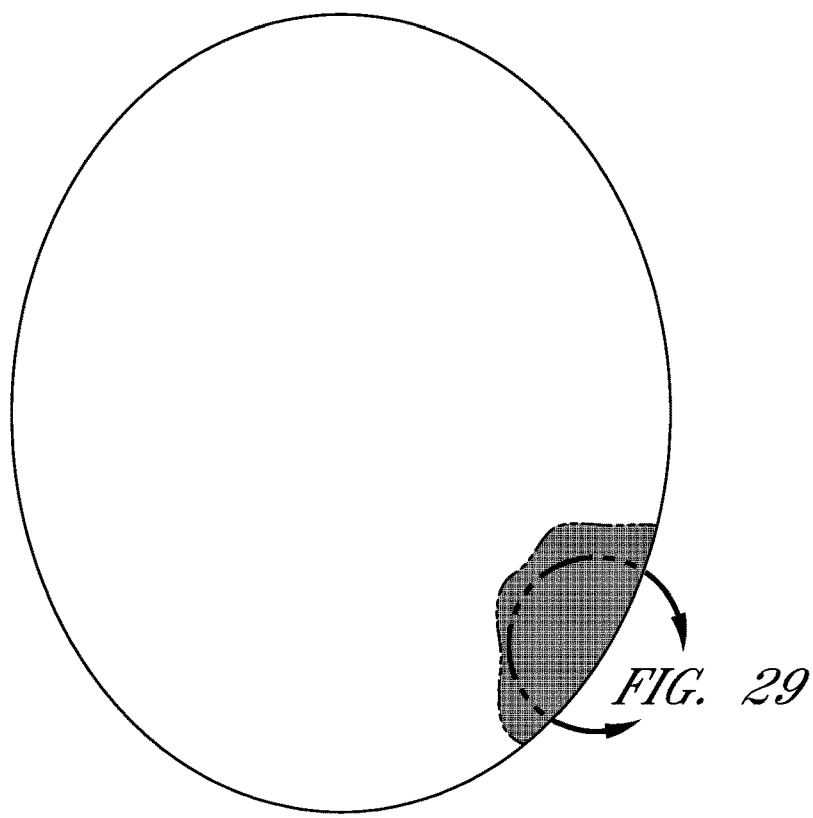
Figure 28:
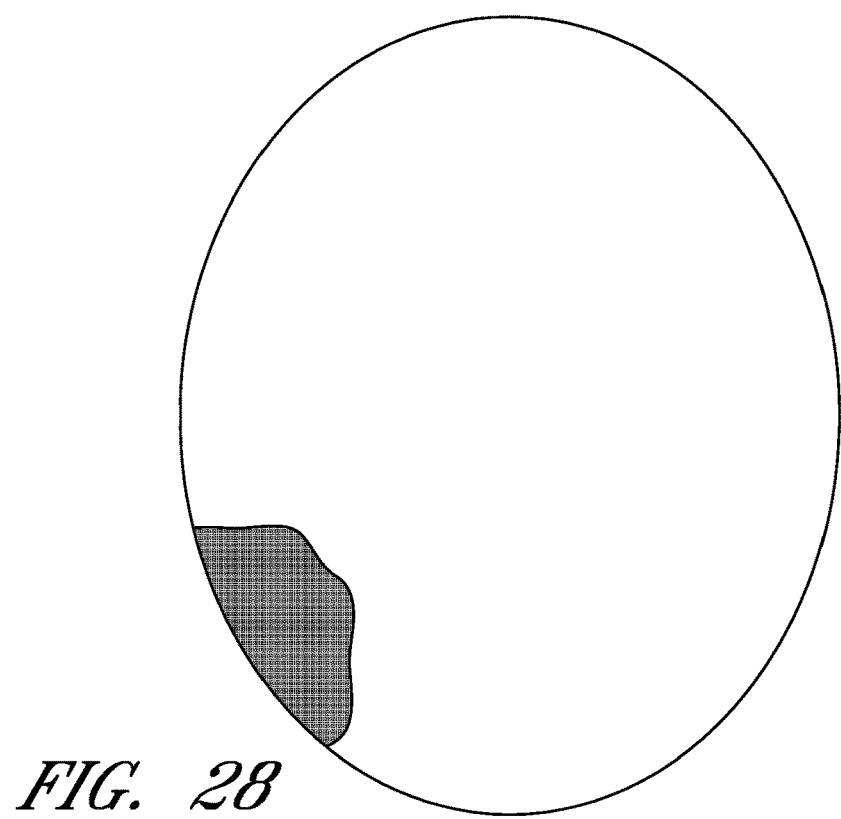
Figure 29:
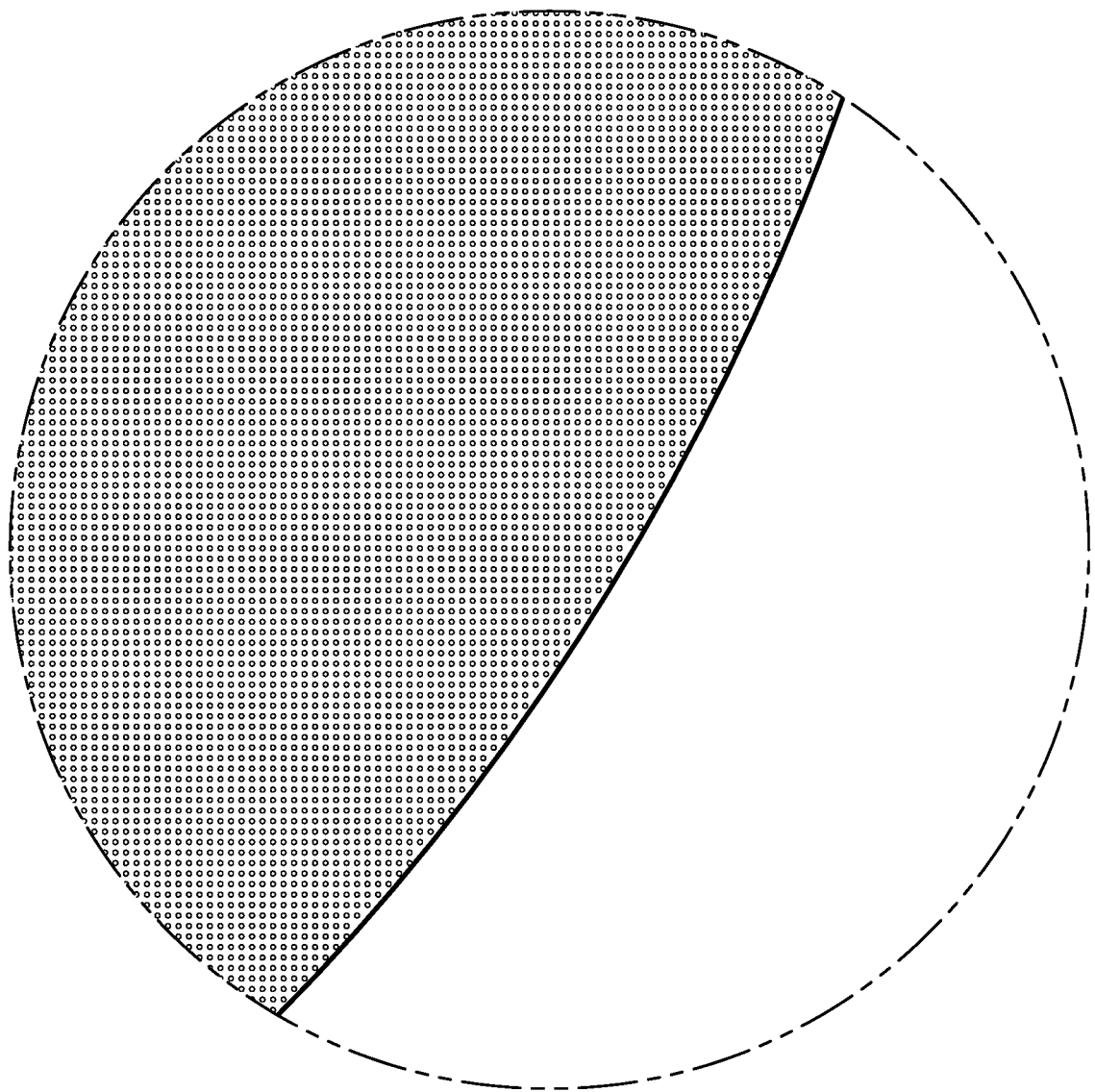
Figure 30:
Figure 31:
Figure 32:
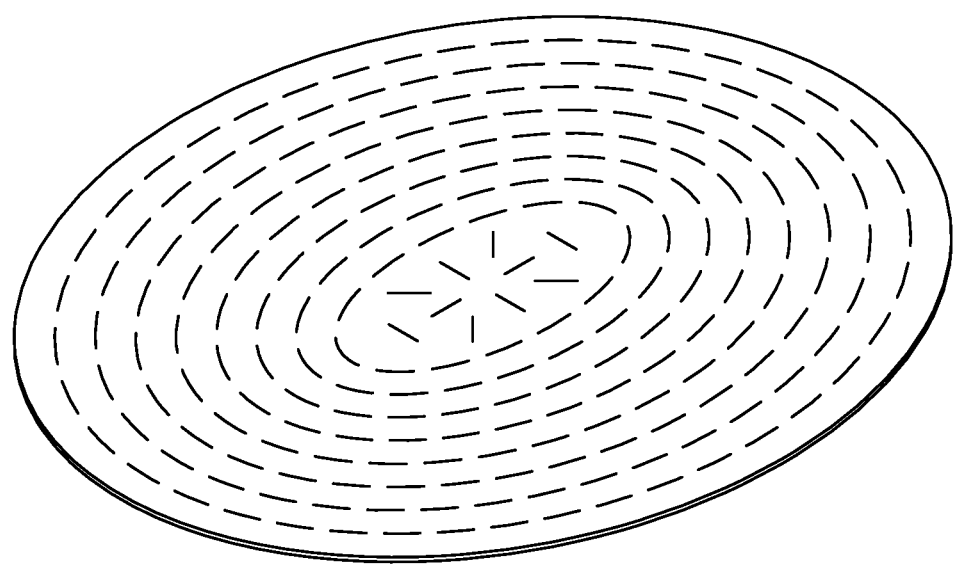
Figure 33:
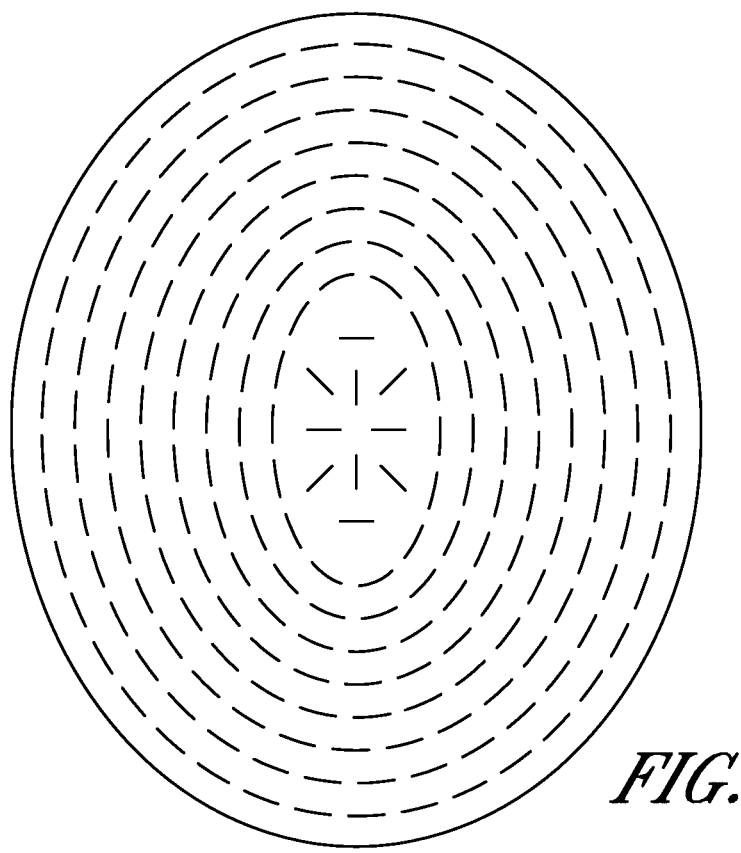
Figure 34:
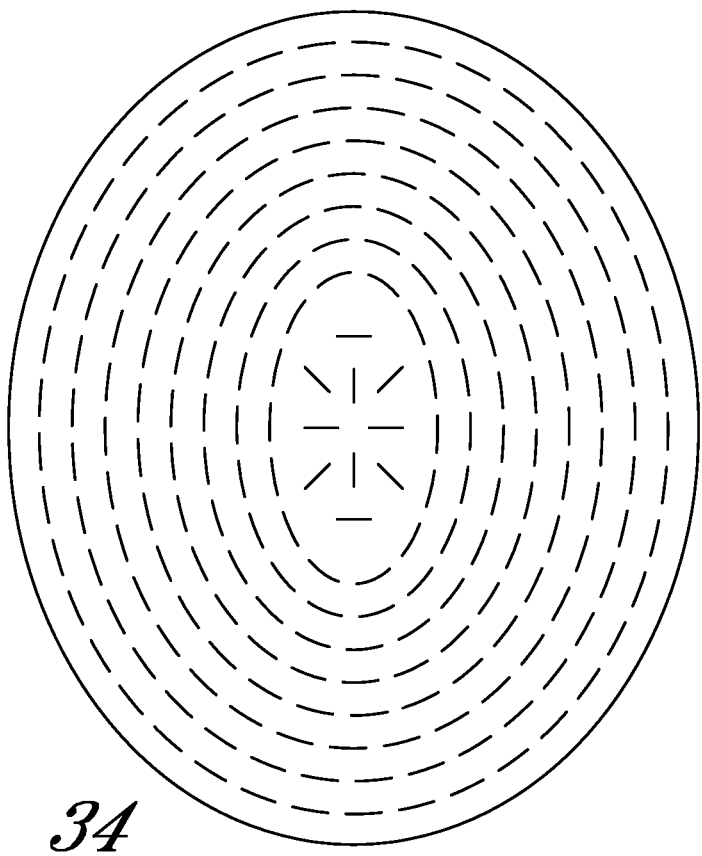
Figure 35:
Figure 36:
Figure 37:
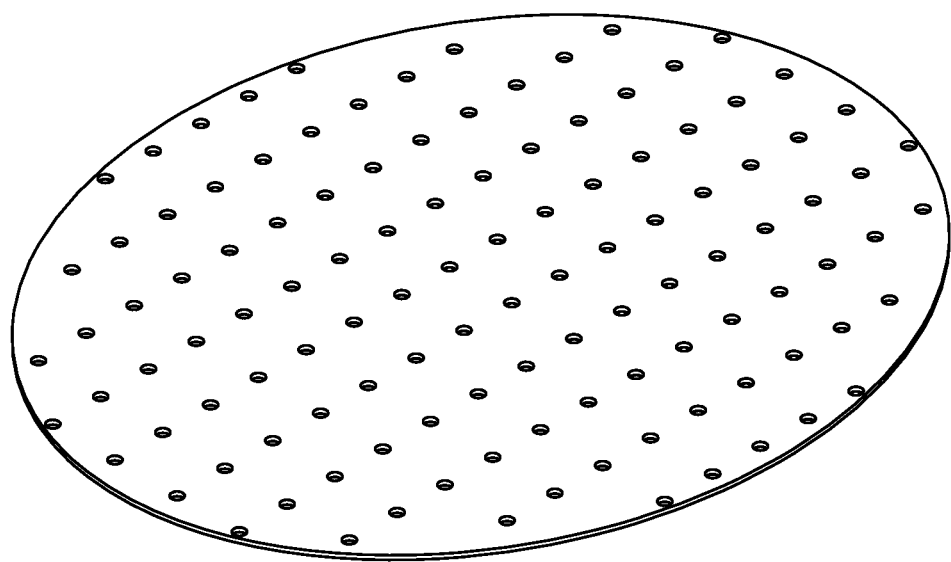
Figure 38:
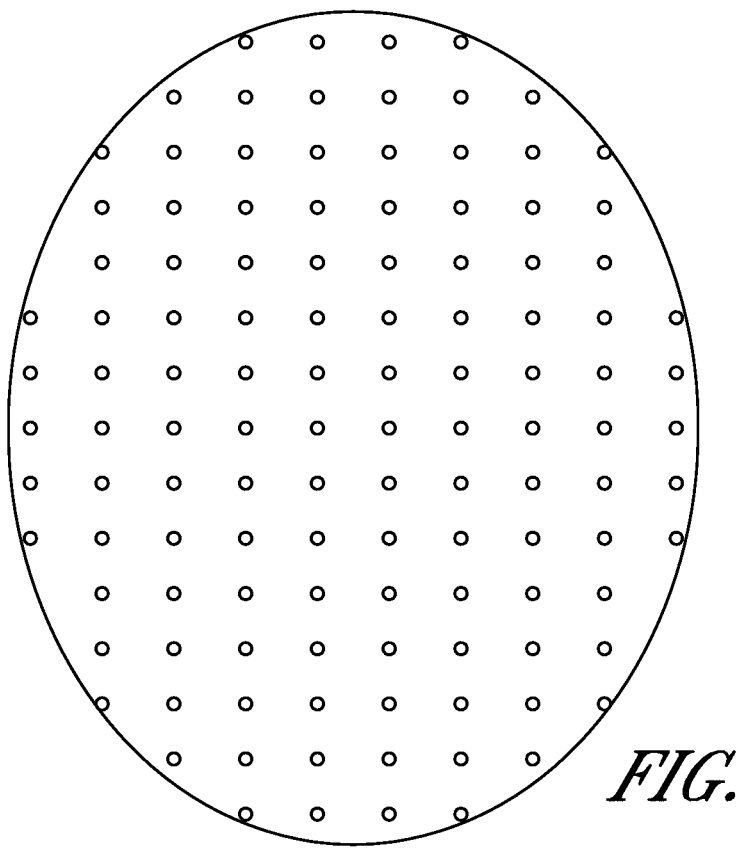
Figure 39:
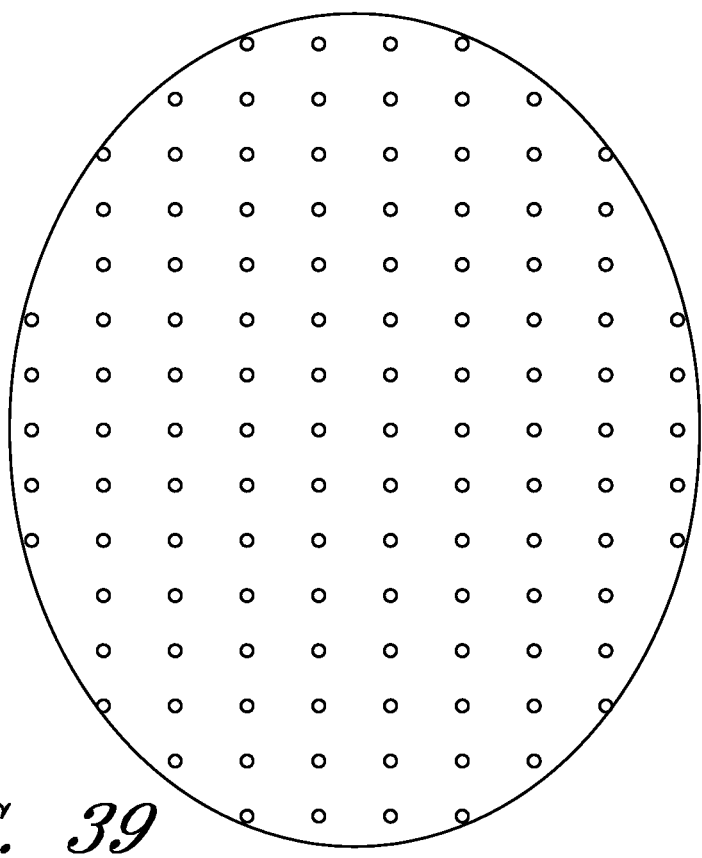
Figure 40:
Figure 41:
Figure 42:
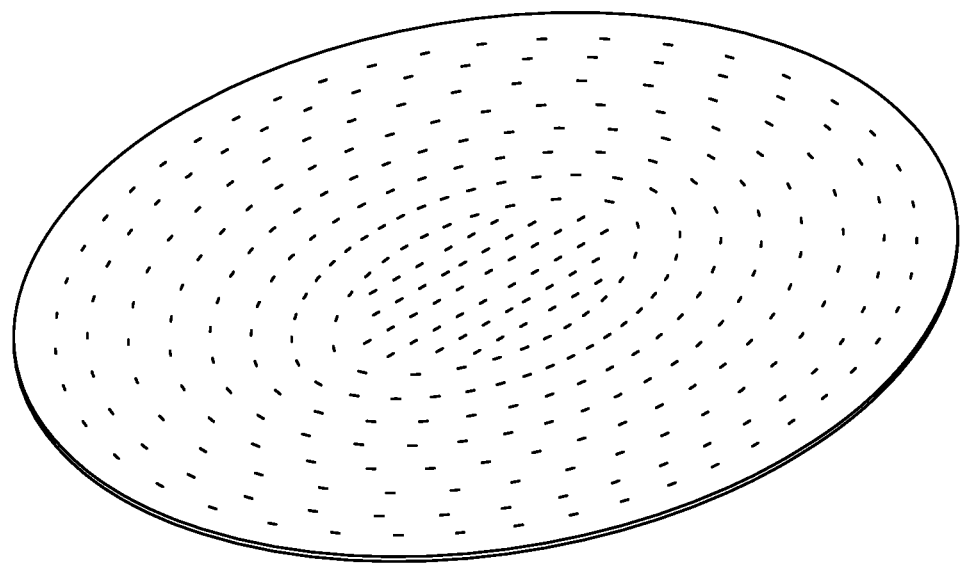
Figure 43:
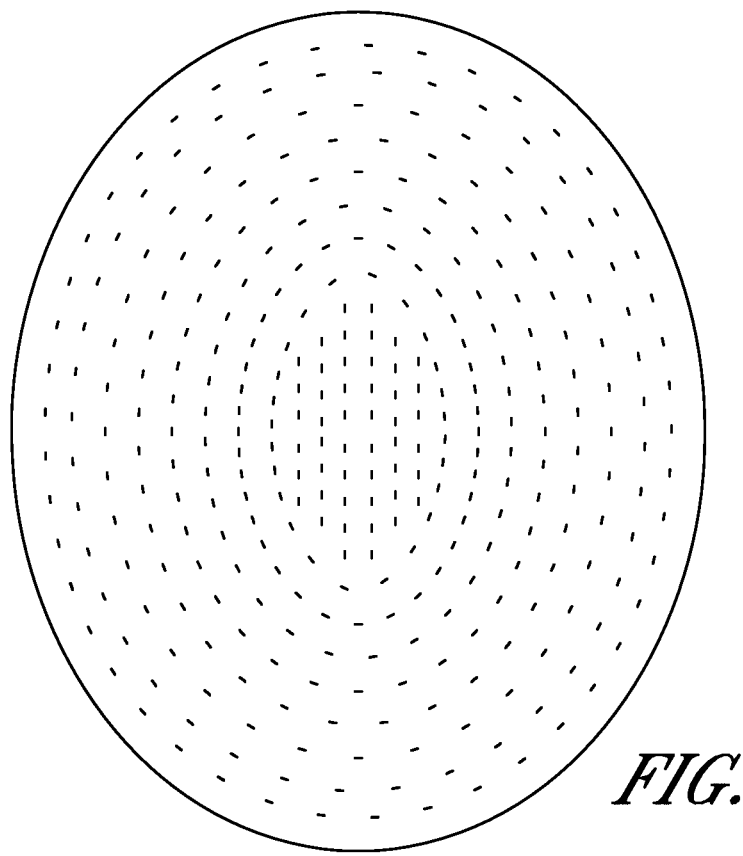
Figure 44:
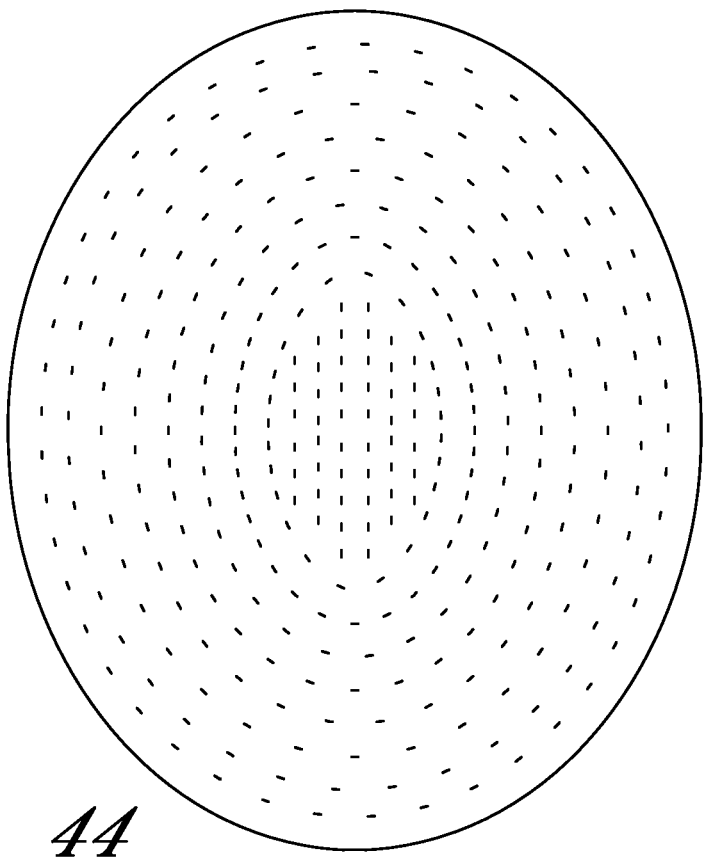
Figure 45:
Figure 46:
Figure 47:
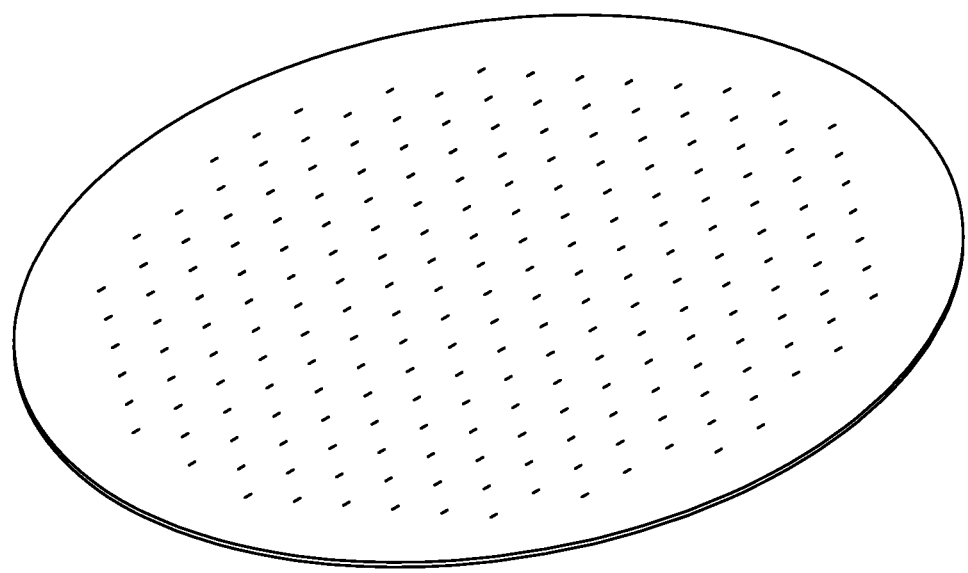
Figure 48:
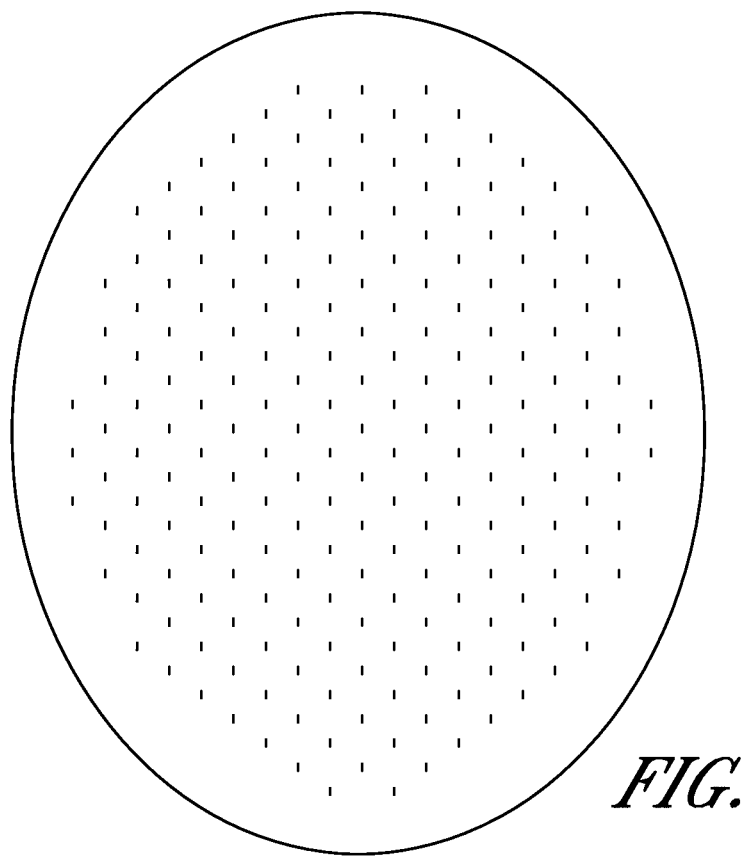
Figure 49:
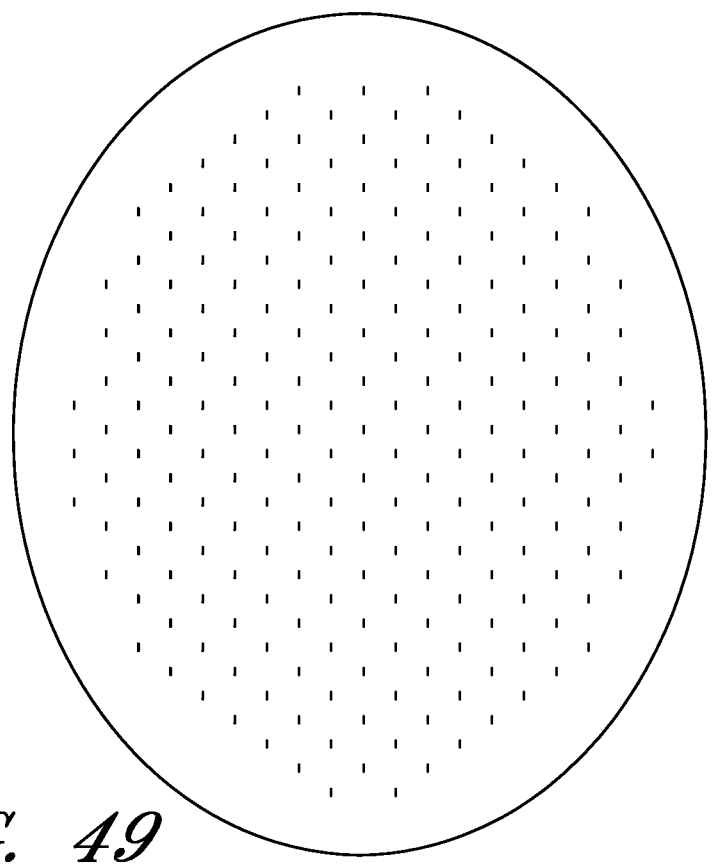
Figure 50:
Figure 51:
Figure 52:
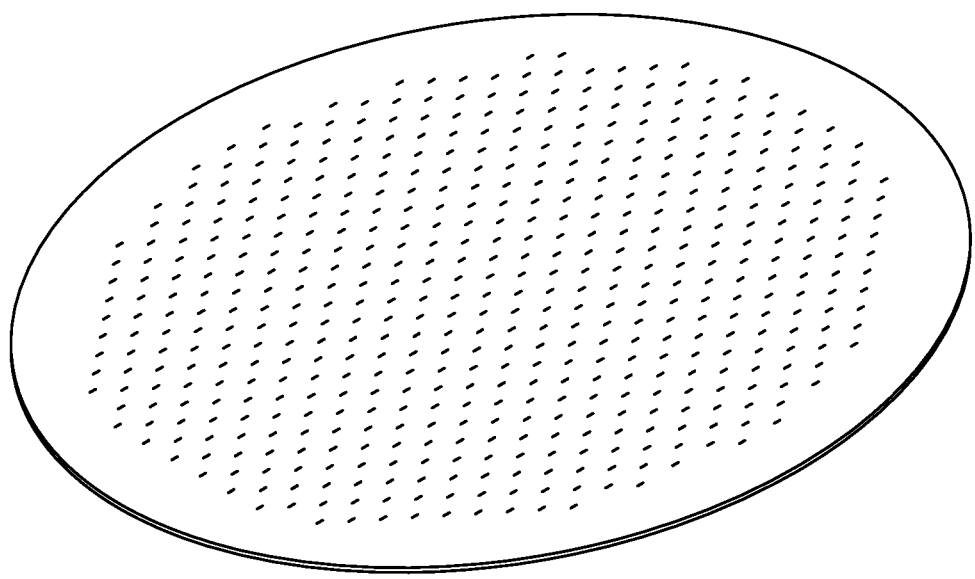
Figure 53:
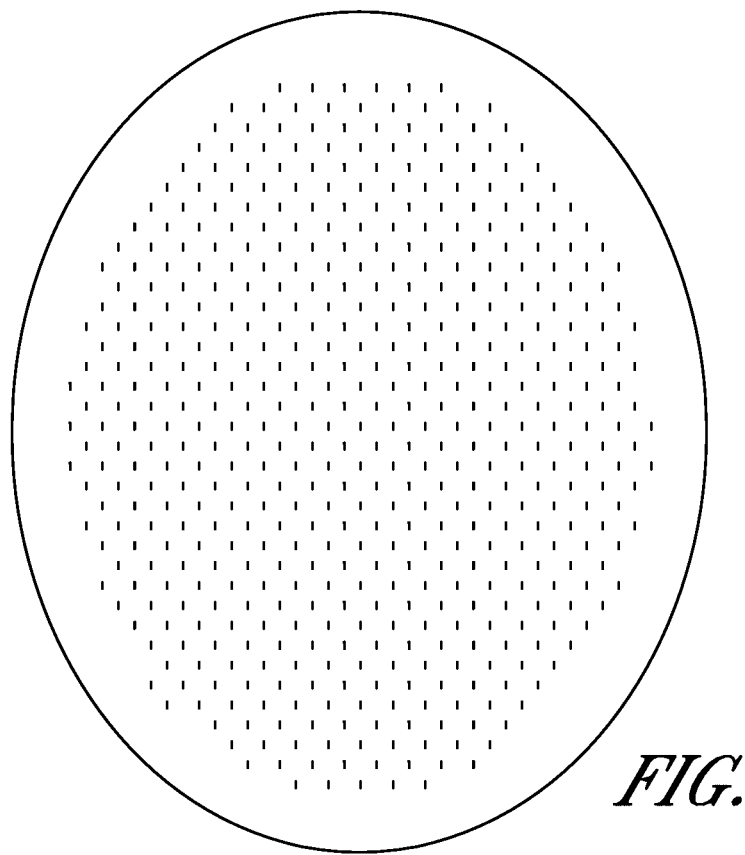
Figure 54:
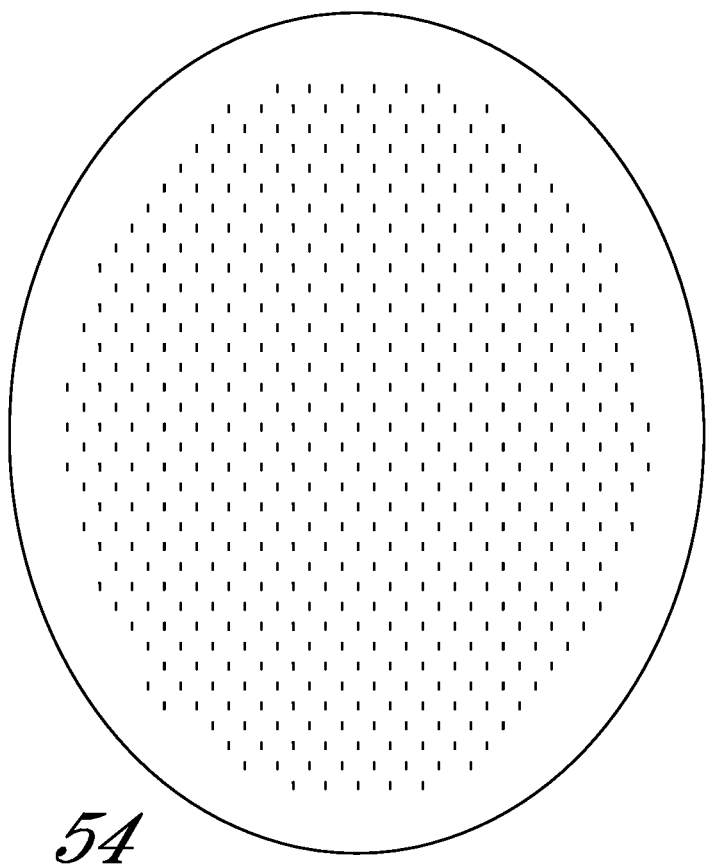
Figure 55:
Figure 56:

With reference to FIGS. 2 and 3, perspective and top views of an embodiment of the porous pad 103 are shown. The pad 103 preferably has one or more perforations made thereon, illustrated for example at arcuate cuts 202, 204, 208, and 210. These cuts may be formed on the pad 103 using any suitable mechanism, including, for example but without, limitation cutting blades, die cutting, or hot wire cutting, and these cuts preferably extend through at least portion of the thickness of the pad 103. The cuts do not need to be continuous, and may consist, for example, of multiple small perforations. In one embodiment, perforations extend entirely across the thickness of the pad 103. In order to ensure that the pad 103 remains structurally intact during handling and use, the cuts made through the pad 103 preferably retain one or more small bridge portions, such as the bridge portion 206.

In one embodiment, the pad 103 has a substantially rectangular shape having a length L, a width W, and a thickness T defined about a major axis X, a minor axis Y, and a vertical axis Z, and has four rounded corners. A first series of arcuate outer cuts 202 may be formed in the pad in an elliptical shape. In the illustrated embodiment, there are four outer cuts 202a, 202b, 202c and 202d, each positioned in one of the quadrants defined by the axes X and Y, with four bridge portions 206 positioned at opposite ends along the major and minor axes. Interior to the outer cuts 202 are a series of arcuate inner cuts 210 also having an elliptical shape similarly shaped to the series of arcuate outer cuts 202. As illustrated, in one embodiment there are four inner cuts 210a, 210b, 210c, 210d also each positioned in one of the quadrants defined by the axes X and Y, with four bridge portions 222 positioned at opposite ends along the major and minor axes.

Located between the outer and inner cuts 202 and 210 are a series of intermediate cuts 204 and 208. From the top view perspective of FIG. 3, an upper arcuate cut 204a and a lower arcuate cut 204b are symmetrically arranged about minor axis Y located at opposite ends of the pad 103. Cuts 204a and 204b extend generally across the width W of the pad, symmetrically about major axis X, with these cuts 204a, 204b having a larger radius of curvature than that of the arcuate cuts 202 near the major axis X. Left and right arcuate cuts 208 are provided between the arcuate cuts 204a, 204b, extending generally length-wise across the pad. As illustrated, there may be four arcuate cuts 208a, 208b, 208c, 208d, each extending generally parallel to the portions of the arcuate cuts 202, 210 that surround them, with bridge portions 220 located on the minor axis Y. It will be appreciated that the shape and number of cuts may be varied, and that there may be more than one series of intermediate cuts between the inner and outer cuts 210, 202.

Advantageously, cuts made on the pad 103 can be used to selectively size the pad 103 to the wound site in which the pad 103 is to be placed. For example, the pad 103 can be sized by removing detachable sections from the pad 103, for example, outer section 218 that surrounds outer cuts 202, inner sections 212a, 212b located between the outer cuts 202 and intermediate cuts 204a and 204b, and inner sections 214a, 214b between the outer cuts 202 and intermediate cuts 208. Although additional and different cuts from the cuts 202, 204, 208, and 210 may be made on the pad 103, these cuts represent examples of types and locations of cuts that can be used to size a pad in a dimensionally-independent manner. Types of cuts that can be made on the pad 103 include, for example, arcuate, circular, ovoid, zigzag, and/or linear cuts. Further, although the cuts shown here are along the length L and width W of the pad, similar cuts may be made along the thickness T of pad 103, such that a thinner pad can be used in a wound site. Cuts may also be made at an angle not aligned with either of the X, Y, or Z axes, for example diagonally across the pad 103.

In use, the pad 103 may be too large for the wound site 110, and may need to be sized by removing the detachable area 218 encompassed by the edges of the pad 103 and the cuts 202 made thereon. For smaller wounds, detachable areas 212a, 212b, 214a, and 214b may all be removed to leave only the detachable areas 216 and 217. In even smaller wounds, the remainder of the pad 103 may be removed to leave only the central detachable area 216. Typically, such sizing can be performed manually, for example using scissors, but such methods incur concomitant disadvantages such as difficulties in manipulating a cutting utensil in a busy operating room, uneven and imprecise cuts, and the possibility of shedding foreign particles into a wound site. Instead, the premade cuts on the pad 103 may be detached by hand or with minimal cutting along the various bridge portions 206, 220, 222.

With continued reference to FIGS. 2-3, certain embodiments permit sizing of a pad 103 in a dimensionally-independent manner. Here, sections from the pad 103 can be detached or cut along the delineations between the various cuts, for example the sections 212a, 212b and 214a, 214b. These cuts 204 and 208 permit sizing of the pad 103 as desired to more closely tailor the actual dimensions of a wound site. For example, sizing a pad 103 for fitting in a wound that is wider on the left side and narrower on the right side may be effectuated by removing a pad section 214a delineated between the cuts 208a, 208b and 202a, 202b. In another example, where the pad 103 is longer along its top portion than the wound site 110, a pad section 212a, delineated between cuts 202a, 202b, and 204a can be removed from one end of the pad 103. In these preceding examples, the outer detachable portion 218 has preferably already been removed, although this is not necessarily required. Consequently, dimensionally-independent sizing of the pad 103 (e.g., modifying the length of the pad without altering the width of the pad, and vice-versa) may be achieved by detaching sections 212, 214 delineated by cuts 204 or 208. Additional detachable sections encompassed by additional cuts so as to permit dimensionally-independent sizing of the pad 103 are contemplated, and the embodiments illustrated herein are not intended to be limiting. Obviously, for smaller wound sites, the removal of symmetric sections of the pad 103 may still be useful, and embodiments of the pad 103 may provide such sections, illustrated here as sections 218, 217, 216. For example, removal of the outer section 218 of the pad 103 along the cuts 202 may be necessary. Similarly, for smaller incisions only the inner section 216 delineated inside cuts 210 may be required.

FIGS. 6-56 illustrate several different embodiments and views of a wound contact layer 105. As stated previously, such a wound contact layer 105 is preferably designed and constructed so as to be minimally adherent to a wound site, and more preferably non adherent to a wound site. In the case of an abdominal wound, the wound contact layer 105 is preferably minimally adherent or non adherent to exposed viscera and other internal organs. The wound contact layer 105 is more preferably constructed from a flexible material, for example polymers such as polyurethane (including Elastollan®), polyethylene, polytetrafluoroethylene, or blends thereof.

The wound contact layer 105 is preferably larger than the foam pad 103, because when used, the wound contact layer 105 may then be tucked around and into a wound site. For example, when used in an abdominal wound, the wound contact layer 105 is preferably inserted into the abdominal cavity between the bowels. Preferably, the wound contact layer 105 is arranged so as to prevent the pad 103 from contacting abdominal viscera and other internal organs, although contact with the edges of the abdominal incision may be acceptable.

In the course of treatment using the system described above, the wound contact layer 105 is preferably permeable, for example provided with openings such as holes, slits, or channels. These openings may be useful in particular in the treatment of abdominal compartment syndrome, where these openings can be used to channel the often-copious amounts of exudate and other fluids that may be produced. In addition to aiding in the removal of exudate and other fluids from a wound site, the openings are useful for transmitting and distributing negative pressure to the wound site. Preferably, the openings are small enough to prevent the in growth of tissue, but large enough to prevent occlusion. Additionally, some embodiments of the wound contact layer 105 can be provided with a microperforated wound contact layer. Different embodiments of the wound contact layer 105 (for example as illustrated in FIGS. 6, 11, 16, 21, 26, 32, 37, 42, 47, 52) may also confer advantages during manufacturing, such as ease of production. Manufacturing of the wound contact layer 105 can entail cutting slits or holes for example with a die or die-cutting knives, rotary perforators, water jets, laser cutting, or ultrasonically.

Treatment of wounds with negative pressure generally requires that the wound be cleaned in a medically-acceptable manner, optionally filled with a wound packing material of some sort (such as foam), sealed with a drape, and connected to a source of negative pressure. The treatment of wounds exposing internal organs, blood vessels, and nerves, and in particular those in the abdominal cavity, may necessitate particular considerations. First, typical wound packing materials such as foam or gauze may desirably not be placed in direct contact with abdominal viscera such as the intestines or stomach, as these materials may undesirably adhere to the viscera. Instead, a non- or minimally-adherent wound contact layer 105, described previously, is preferably placed in the abdominal cavity or wound site 110. This wound contact layer 105 is preferably cut to size (if necessary), and tucked between the viscera and the abdominal fascia, with any excess material folded up over itself to avoid trapping any of the abdominal contents. Subsequently, the foam pad 103, after being sized as described above, is placed over the wound contact layer and preferably toward the middle of the wound site 110. A drape 107, again as described above, is cut to size (if necessary) and preferably placed such that it overlaps onto at least a portion of healthy skin surrounding the wound site 110. In some cases, if one drape 107 is insufficient, additional drapes may be provided; these are preferably overlapped at least partially so as to permit a secure seal to be made. Preferably, the drape 107 is provided with an adhesive layer on its underside, which may be protected by a backing layer. Such a backing layer is preferably removed before use so as to permit the drape 107 to be adhered to the skin surrounding the wound site as well as to the foam pad 103. An aperture 109 may then be made through the drape 107, although some embodiments may comprise a drape 107 supplied with one ore more pre-made aperture or apertures 109. A conduit 112 connected to a source of negative pressure may then be connected to the aperture 109, or, in some embodiments, under a side of the drape 107, such that a fluidic connection between the wound site 110 and the source of negative pressure is created. The fluidic connection permits the therapeutic application of negative pressure to the wound site 110, and may be applied as necessary until the wound site 110 has reached a desired level of healing or until another surgical intervention is required.

Of course, the foregoing description is that of certain features, aspects and advantages of the present invention, to which various changes and modifications can be made without departing from the spirit and scope of the present invention. Moreover, the negative pressure treatment system disclosed herein need not feature all of the objects, advantages, features and aspects discussed above. Those of skill in the art will recognize that the invention can be embodied or carried out in a manner that achieves or optimizes one advantage or a group of advantages as taught herein without necessarily achieving other objects or advantages as may be taught or suggested herein. For example, in some embodiments the pad 103 can be used without the wound contact layer 105 and/or drape 107. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed negative pressure treatment system.

What is claimed is:

1. A porous pad for the treatment of wounds using negative pressure, wherein the porous pad comprises:
   a porous material configured to channel wound exudate from a wound site and negative pressure to the wound site;
   a generally planar shape with a thickness less than a width and a length, wherein the length is greater than the width and the generally planar shape has a major axis extending along the length and a minor axis extending along the width, the major and minor axes both bisecting the porous pad;
   a first plurality of arcuate cuts or perforations extending through at least a portion of the thickness of the porous pad, the first plurality of arcuate cuts or perforations comprising a first arcuate cut or perforation arranged in series with a second arcuate cut or perforation, a first bridge portion disposed on the minor axis and between the first arcuate cut or perforation and the second arcuate cut or perforation, the first arcuate cut or perforation, the first bridge portion, and the second arcuate cut or perforation defining a first continuous arcuate shape;
   a second plurality of arcuate cuts or perforations extending through at least a portion of the thickness of the porous pad, the second plurality of arcuate cuts or perforations disposed between the first continuous arcuate shape and the major axis, the second plurality of arcuate cuts or perforations comprising a third arcuate cut or perforation arranged in series with a fourth arcuate cut or perforation, a second bridge portion disposed on the minor axis and between the third arcuate cut or perforation and the fourth arcuate cut or perforation, the third arcuate cut or perforation, the second bridge portion, and the fourth arcuate cut or perforation defining a second continuous arcuate shape, wherein the third arcuate cut or perforation extends continuously from the second bridge portion to a third bridge portion disposed on the major axis, and the fourth arcuate cut or perforation extends continuously from the second bridge portion to a fourth bridge portion disposed on the major axis; and a corresponding third arcuate cut or perforation disposed symmetrically across the major axis of the porous pad from the third arcuate cut or perforation, a corresponding fourth arcuate cut or perforation disposed symmetrically across the major axis of the porous pad from the fourth arcuate cut or perforation, and a fifth bridge portion disposed on the minor axis and between the corresponding third arcuate cut or perforation and the corresponding fourth arcuate cut or perforation, wherein the corresponding third arcuate cut or perforation extends continuously from the fifth bridge portion disposed on the minor axis to the third bridge portion disposed on the major axis, and the corresponding fourth arcuate cut or perforation extends continuously from the fifth bridge portion disposed on the minor axis to the fourth bridge portion disposed on the major axis.

2. The porous pad of claim 1, further comprising:
a third plurality of arcuate cuts or perforations extending through at least a portion of the thickness of the porous pad, the third plurality of arcuate cuts or perforations being substantially parallel to the first plurality of arcuate cuts or perforations to define a third continuous arcuate shape, wherein the third plurality of arcuate cuts or perforations is interposed between the first plurality of arcuate cuts or perforations and an edge of the generally planar shape.

3. The porous pad of claim 2, wherein the third continuous arcuate shape comprises a sixth bridge portion, wherein the sixth bridge portion is disposed on the minor axis.

4. The porous pad of claim 1, further comprising a corresponding first continuous arcuate shape symmetrically disposed across the major axis of the porous pad from the first continuous arcuate shape.

5. The porous pad of claim 4, wherein the minor axis substantially bisects the first continuous arcuate shape and the corresponding first continuous arcuate shape.

6. The porous pad of claim 1, wherein the porous pad comprises an open-celled, reticulated foam.

7. The porous pad of claim 1, further comprising an upper arcuate cut, the third arcuate cut or perforation disposed between the minor axis and the upper arcuate cut.

8. The porous pad of claim 7, wherein the upper arcuate cut is bisected by the major axis.

9. The porous pad of claim 7, further comprising a lower arcuate cut disposed symmetrically across the minor axis of the porous pad from the upper arcuate cut.

10. The porous pad of claim 1, wherein each of the first bridge portion, the second bridge portion, and the fifth bridge portion is bisected by the minor axis.

11. A porous pad for the treatment of wounds using negative pressure, wherein the porous pad comprises:
a porous material configured to channel wound exudate from a wound site and negative pressure to the wound site;
a generally planar shape with a thickness less than a width and a length, wherein the length is greater than the width and the generally planar shape has a major axis extending along the length and a minor axis extending along the width, the major and minor axes both bisecting the porous pad;
a first arcuate cut extending continuously from a first bridge portion disposed on the minor axis to a second bridge portion disposed on the major axis;
a second arcuate cut extending continuously from the second bridge portion to a third bridge portion disposed on the minor axis, the second arcuate cut disposed symmetrically across the major axis from the first arcuate cut;
a third arcuate cut extending continuously from the third bridge portion to a fourth bridge portion disposed on the major axis; and
a fourth arcuate cut extending continuously from the fourth bridge portion to the first bridge portion, the fourth arcuate cut disposed symmetrically across the major axis from the third arcuate cut, wherein a continuous arcuate shape is defined by the first bridge portion, the first arcuate cut, the second bridge portion, the second arcuate cut, the third bridge portion, the third arcuate cut, the fourth bridge portion, and the fourth arcuate cut.

12. The porous pad of claim 11, further comprising an upper arcuate cut, the first arcuate cut or perforation disposed between the minor axis and the upper arcuate cut.

13. The porous pad of claim 12, further comprising a lower arcuate cut disposed symmetrically across the minor axis of the porous pad from the upper arcuate cut.

14. The porous pad of claim 11, wherein the continuous arcuate shape is elliptical.

* * * * *